(12) United States Patent
Tamarkin et al.

(10) Patent No.: US 7,704,518 B2
(45) Date of Patent: *Apr. 27, 2010

(54) FOAMABLE VEHICLE AND PHARMACEUTICAL COMPOSITIONS THEREOF

(75) Inventors: Dov Tamarkin, Maccabim (IL); Doron Friedman, Karmei Yosef (IL); Meir Eini, Ness Ziona (IL); Alex Besonov, Rehovot (IL)

(73) Assignee: Foamix, Ltd., Ness Ziona (IL)

( * ) Notice: Subject to any disclaimer, the term of this patent is extended or adjusted under 35 U.S.C. 154(b) by 226 days.

This patent is subject to a terminal disclaimer.

(21) Appl. No.: 11/430,599

(22) Filed: May 9, 2006

(65) Prior Publication Data

US 2006/0275218 A1 Dec. 7, 2006

Related U.S. Application Data

(63) Continuation-in-part of application No. 10/835,505, filed on Apr. 28, 2004.

(60) Provisional application No. 60/679,020, filed on May 9, 2005, provisional application No. 60/784,793, filed on Mar. 21, 2006.

(51) Int. Cl.
- *A01N 25/16* (2006.01)
- *A61K 47/00* (2006.01)
- *A61K 47/30* (2006.01)
- *A61K 47/32* (2006.01)

(52) U.S. Cl. .................. 424/405; 514/772.2; 514/772.3; 514/772.6; 514/776; 514/778; 514/945

(58) Field of Classification Search ....................... None
See application file for complete search history.

(56) References Cited

U.S. PATENT DOCUMENTS

| | | | |
|---|---|---|---|
| 1,924,972 A | 8/1933 | Beckert | |
| 2,085,733 A | 7/1937 | Bird | |
| 2,390,921 A | 12/1945 | Clark | |
| 2,524,590 A | 10/1950 | Boe | |
| 2,586,287 A | 2/1952 | Apperson | |
| 2,617,754 A | 11/1952 | Neely | |
| 2,968,628 A | 1/1961 | Reed | |
| 3,062,715 A | 11/1962 | Reese | |
| 3,092,255 A | 6/1963 | Hohman | |
| 3,092,555 A | 6/1963 | Horn | |
| 3,141,821 A | 7/1964 | Compeau | |
| 3,142,420 A | 7/1964 | Gawthrop | |
| 3,144,386 A | 8/1964 | Brighttenback | |
| 3,154,075 A | 10/1964 | Weckesser | |
| 3,178,352 A | 4/1965 | Erickson | |
| 3,236,457 A | 2/1966 | Kennedy et al. | |
| 3,244,589 A | 4/1966 | Sunnen | |
| 3,252,859 A | 5/1966 | Silver | |
| 3,261,695 A | 7/1966 | Sienciewicz | |
| 3,263,869 A | 8/1966 | Corsette | |
| 3,301,444 A | 1/1967 | Wittke | |
| 3,303,970 A | 2/1967 | Breslau et al. | |
| 3,330,730 A | 7/1967 | Hernaadez | |
| 3,369,034 A | 2/1968 | Chalmers | |
| 3,384,541 A | 5/1968 | Clark et al. | |
| 3,395,215 A | 7/1968 | Warren | |
| 3,401,849 A | 9/1968 | Weber, III | |
| 3,419,658 A | 12/1968 | Amsdon | |
| 3,559,890 A | 2/1971 | Brooks et al. | |
| 3,561,262 A | 2/1971 | Borocki | |
| 3,574,821 A | 4/1971 | Pfirrmann et al. | |
| 3,577,518 A | 5/1971 | Shepherd | |
| 3,751,562 A | 8/1973 | Nichols | |
| 3,770,648 A | 11/1973 | Mackes | |
| 3,787,566 A | 1/1974 | Gauvreau | |
| 3,882,228 A | 5/1975 | Boncey et al. | |
| 3,886,084 A | 5/1975 | Vassiliades | |
| 3,890,305 A | 6/1975 | Weber et al. | |
| 3,912,665 A | 10/1975 | Spitzer et al. | |
| 3,923,970 A | 12/1975 | Breuer | |
| 3,929,985 A * | 12/1975 | Webb, Jr. ..................... | 424/45 |
| 3,959,160 A | 5/1976 | Horsler et al. | |
| 3,962,150 A | 6/1976 | Viola | |
| 3,966,090 A | 6/1976 | Prussin et al. | |
| 3,970,584 A * | 7/1976 | Hart et al. ..................... | 516/10 |
| 3,993,224 A | 11/1976 | Harrison | |
| 3,997,467 A | 12/1976 | Jederstrom et al. | |
| 4,001,442 A | 1/1977 | Stahlberger et al. | |

(Continued)

FOREIGN PATENT DOCUMENTS

DE 933486 9/1955

(Continued)

OTHER PUBLICATIONS

International Search Report from PCT/IB2006/003519, Mailed Dec. 3, 2007.

(Continued)

*Primary Examiner*—Ernst V Arnold
(74) *Attorney, Agent, or Firm*—Wilmer Cutler Pickering Hale and Dorr LLP

(57) ABSTRACT

A hygroscopic pharmaceutical composition includes at least one hygroscopic substance at a concentration sufficient to provide an Aw value of at least 0.9 and an antiinfective agent. A foamble pharmaceutical carrier includes about 50% to about 98% of a polar solvent selected from the group consisting of a polyol and PEG; 0% to about 48% of a secondary polar solvent; about 0.2% to about 5% by weight of a surface-active agent; about 0.01% to about 5% by weight of at least one polymeric agent; and a liquefied or compressed gas propellant at a concentration of about 3% to about 25% by weight of the total composition.

75 Claims, 4 Drawing Sheets

U.S. PATENT DOCUMENTS

| | | |
|---|---|---|
| 4,019,657 A | 4/1977 | Spitzer et al. |
| 4,110,426 A | 8/1978 | Barnhurst et al. |
| 4,124,149 A | 11/1978 | Spitzer et al. |
| 4,145,411 A | 3/1979 | Mende |
| 4,160,827 A | 7/1979 | Cho et al. |
| 4,213,979 A | 7/1980 | Levine |
| 4,214,000 A | 7/1980 | Papa |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,292,326 A | 9/1981 | Nazzaro-Porro et al. |
| 4,299,826 A | 11/1981 | Luedders |
| 4,323,694 A | 4/1982 | Scala, Jr. |
| 4,385,161 A | 5/1983 | Caunt et al. |
| 4,386,104 A | 5/1983 | Nazzaro-Porro |
| 4,447,486 A | 5/1984 | Hoppe et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,574,052 A | 3/1986 | Gupte et al. |
| 4,576,961 A | 3/1986 | Lorck et al. |
| 4,627,973 A | 12/1986 | Moran et al. |
| 4,628,063 A | 12/1986 | Haines et al. |
| 4,672,078 A | 6/1987 | Sakai et al. |
| 4,673,569 A | 6/1987 | Shernov et al. |
| 4,741,855 A | 5/1988 | Grote et al. |
| 4,752,465 A | 6/1988 | Mackles |
| 4,784,842 A | 11/1988 | London et al. |
| 4,792,062 A | 12/1988 | Goncalves et al. |
| 4,804,674 A | 2/1989 | Curtis-Prior |
| 4,808,388 A | 2/1989 | Beutler et al. |
| 4,822,613 A | 4/1989 | Rodero |
| 4,827,378 A | 5/1989 | Gillan et al. |
| 4,836,217 A | 6/1989 | Fischer et al. |
| 4,837,378 A | 6/1989 | Borgman |
| 4,847,068 A | 7/1989 | Dole et al. |
| 4,863,900 A | 9/1989 | Pollock et al. |
| 4,873,078 A | 10/1989 | Edmundson et al. |
| 4,874,794 A | 10/1989 | Katz |
| 4,877,805 A | 10/1989 | Kligman |
| 4,885,282 A | 12/1989 | Thornfeldt |
| 4,897,262 A | 1/1990 | Nandagiri et al. |
| 4,913,893 A | 4/1990 | Varco |
| 4,956,049 A | 9/1990 | Bernheim et al. |
| 4,957,732 A | 9/1990 | Grollier et al. |
| 4,963,351 A | 10/1990 | Weston |
| 4,981,677 A | 1/1991 | Thau |
| 4,981,679 A | 1/1991 | Briggs et al. |
| 4,981,845 A | 1/1991 | Pereira et al. |
| 4,992,478 A | 2/1991 | Geria |
| 5,002,680 A | 3/1991 | Schmidt et al. |
| 5,007,556 A | 4/1991 | Lover |
| 5,015,471 A | 5/1991 | Birtwistle et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,087,618 A | 2/1992 | Bodor |
| 5,089,252 A | 2/1992 | Grollier |
| 5,094,853 A | 3/1992 | Hagarty |
| 5,100,917 A | 3/1992 | Flynn et al. |
| 5,104,645 A | 4/1992 | Cardin et al. |
| 5,130,121 A | 7/1992 | Kopolow et al. |
| 5,133,972 A | 7/1992 | Ferrini et al. |
| 5,135,915 A | 8/1992 | Czarniecki et al. |
| 5,143,717 A | 9/1992 | Davis |
| 5,156,765 A | 10/1992 | Smrt |
| 5,164,357 A | 11/1992 | Bartman et al. |
| 5,167,950 A | 12/1992 | Linds |
| 5,171,577 A | 12/1992 | Griat et al. |
| 5,196,405 A | 3/1993 | Packman |
| 5,204,093 A | 4/1993 | Victor |
| 5,208,031 A | 5/1993 | Kelly |
| 5,217,707 A | 6/1993 | Szabo et al. |
| 5,230,897 A | 7/1993 | Griffin et al. |
| 5,254,334 A | 10/1993 | Ramirez et al. |
| 5,262,407 A | 11/1993 | Leveque et al. |
| 5,279,819 A | 1/1994 | Hayes |
| 5,300,286 A | 4/1994 | Gee |
| 5,301,841 A | 4/1994 | Fuchs et al. |
| 5,308,643 A | 5/1994 | Osipow et al. |
| 5,314,904 A | 5/1994 | Egidio et al. |
| 5,326,557 A | 7/1994 | Glover et al. |
| 5,352,437 A | 10/1994 | Nakagawa |
| 5,380,761 A | 1/1995 | Szabo |
| 5,384,308 A | 1/1995 | Henkin |
| 5,385,943 A | 1/1995 | Nazzaro-Porro |
| 5,411,992 A | 5/1995 | Eini et al. |
| 5,422,361 A | 6/1995 | Munayyer et al. |
| 5,429,815 A | 7/1995 | Faryniarz |
| 5,435,996 A | 7/1995 | Glover et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A * | 7/1996 | Trinh et al. ............... 510/101 |
| 5,545,401 A | 8/1996 | Shanbrom |
| 5,567,420 A | 10/1996 | McEleney et al. |
| 5,578,315 A | 11/1996 | Chien et al. |
| 5,589,157 A | 12/1996 | Hatfield |
| 5,589,515 A | 12/1996 | Suzuki et al. |
| 5,603,940 A | 2/1997 | Candau et al. |
| 5,605,679 A | 2/1997 | Hansenne et al. |
| 5,614,171 A | 3/1997 | Clavenna et al. |
| 5,635,469 A | 6/1997 | Fowler et al. |
| 5,641,480 A | 6/1997 | Vermeer |
| 5,645,842 A | 7/1997 | Gruning et al. |
| 5,650,554 A | 7/1997 | Moloney |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,700,396 A | 12/1997 | Suzuki et al. |
| 5,716,611 A | 2/1998 | Oshlack et al. |
| 5,719,197 A | 2/1998 | Kanios |
| 5,730,964 A | 3/1998 | Waldstreicher |
| 5,733,558 A | 3/1998 | Breton et al. |
| 5,753,245 A | 5/1998 | Fowler et al. |
| 5,759,520 A | 6/1998 | Sachetto |
| 5,759,579 A | 6/1998 | Singh et al. |
| 5,767,104 A | 6/1998 | Bar-Shalom et al. |
| 5,783,202 A | 7/1998 | Tomlinson et al. |
| 5,792,922 A | 8/1998 | Moloney |
| 5,804,546 A | 9/1998 | Hall et al. |
| 5,817,322 A | 10/1998 | Xu |
| 5,824,650 A * | 10/1998 | De Lacharriere et al. ...... 514/15 |
| 5,833,960 A | 11/1998 | Gers-Barlag et al. |
| 5,837,270 A | 11/1998 | Burgess |
| 5,840,744 A | 11/1998 | Borgman |

| | | | | | | |
|---|---|---|---|---|---|---|
| 5,856,452 | A | 1/1999 | Moloney et al. | 6,649,574 B2 | 11/2003 | Cardis et al. |
| 5,866,040 | A | 2/1999 | Nakama et al. | 6,672,483 B1 | 1/2004 | Roy et al. |
| 5,871,720 | A | 2/1999 | Gutierrez et al. | 6,730,288 B2 | 5/2004 | Abram |
| 5,877,216 | A | 3/1999 | Place | 6,753,167 B2 | 6/2004 | Moloney et al. |
| 5,879,469 | A | 3/1999 | Avram et al. | 6,765,001 B2 | 7/2004 | Gans et al. |
| 5,885,581 | A | 3/1999 | Massand | 6,777,591 B1 | 8/2004 | Chaudhary |
| 5,889,028 | A | 3/1999 | Sandborn | 6,902,737 B2 | 6/2005 | Quemin et al. |
| 5,891,458 | A | 4/1999 | Britton | 6,946,120 B2 | 9/2005 | Wai-Chiu So et al. |
| 5,902,574 | A | 5/1999 | Stoner et al. | 7,029,659 B2 | 4/2006 | Abram et al. |
| 5,902,789 | A | 5/1999 | Stoltz | 7,137,536 B2 | 11/2006 | Walters et al. |
| 5,911,981 | A | 6/1999 | Dahms | 7,235,251 B2 | 6/2007 | Hamer et al. |
| 5,914,310 | A | 6/1999 | Li et al. | 7,270,828 B2 | 9/2007 | Masuda et al. |
| 5,922,331 | A | 7/1999 | Mausner | 2001/0006654 A1 | 7/2001 | Cannell et al. |
| 5,948,682 | A | 9/1999 | Moloney | 2002/0032171 A1 | 3/2002 | Chen et al. |
| 5,951,993 | A | 9/1999 | Scholz et al. | 2002/0035046 A1 | 3/2002 | Lukenbach et al. |
| 5,952,392 | A | 9/1999 | Katz | 2002/0045659 A1* | 4/2002 | Michelet et al. ............. 514/557 |
| 5,961,957 | A | 10/1999 | McAnalley | 2002/0048798 A1 | 4/2002 | Avery et al. |
| 5,972,310 | A | 10/1999 | Sachetto | 2002/0072544 A1 | 6/2002 | Miller et al. |
| 5,993,846 | A | 11/1999 | Friedman et al. | 2002/0098215 A1 | 7/2002 | Douin et al. |
| 6,019,967 | A | 2/2000 | Breton et al. | 2002/0117516 A1 | 8/2002 | Lasserre et al. |
| 6,033,647 | A | 3/2000 | Touzan et al. | 2002/0134376 A1 | 9/2002 | Castro et al. |
| 6,042,848 | A | 3/2000 | Lawyer et al. | 2002/0143188 A1 | 10/2002 | Garvey et al. |
| 6,045,779 | A | 4/2000 | Mueller et al. | 2002/0198136 A1 | 12/2002 | Mak et al. |
| 6,071,536 | A | 6/2000 | Suzuki | 2003/0006193 A1 | 1/2003 | Ikeda et al. |
| 6,080,394 | A | 6/2000 | Lin | 2003/0031693 A1 | 2/2003 | Breton et al. |
| 6,087,317 | A | 7/2000 | Gee | 2003/0215472 A1 | 11/2003 | Bonda et al. |
| 6,090,772 | A | 7/2000 | Kaiser et al. | 2004/0018228 A1 | 1/2004 | Fischell et al. |
| 6,093,408 | A | 7/2000 | Hasenoehrl et al. | 2004/0028752 A1 | 2/2004 | Kamm et al. |
| 6,113,888 | A | 9/2000 | Castro et al. | 2004/0038912 A1 | 2/2004 | Michelet et al. |
| 6,116,466 | A | 9/2000 | Gueret et al. | 2004/0053797 A1 | 3/2004 | Chen et al. |
| 6,121,210 | A | 9/2000 | Taylor | 2004/0063787 A1 | 4/2004 | Villanueva |
| 6,126,920 | A | 10/2000 | Jones et al. | 2004/0078896 A1 | 4/2004 | Hellyer et al. |
| 6,140,355 | A | 10/2000 | Egidio et al. | 2004/0151671 A1 | 8/2004 | Abram et al. |
| 6,146,645 | A | 11/2000 | Deckers et al. | 2004/0191196 A1 | 9/2004 | Tamarkin |
| 6,171,347 | B1 | 1/2001 | Kunz et al. | 2004/0192754 A1 | 9/2004 | Shapira et al. |
| 6,180,669 | B1 | 1/2001 | Tamarkin | 2004/0197276 A1 | 10/2004 | Takase et al. |
| 6,183,762 | B1 | 2/2001 | Deckers et al. | 2004/0219122 A1 | 11/2004 | Masuda et al. |
| 6,186,367 | B1 | 2/2001 | Harrold | 2004/0234475 A1 | 11/2004 | Lannibois-Drean |
| 6,187,290 | B1 | 2/2001 | Gilchrist et al. | 2004/0241099 A1 | 12/2004 | Popp et al. |
| 6,210,742 | B1 | 4/2001 | Deckers et al. | 2004/0253275 A1 | 12/2004 | Eini et al. |
| 6,221,381 | B1 | 4/2001 | Shelford et al. | 2004/0265240 A1 | 12/2004 | Tamarkin et al. |
| 6,224,888 | B1 | 5/2001 | Vatter | 2005/0013853 A1 | 1/2005 | Gil-Ad et al. |
| 6,231,837 | B1 | 5/2001 | Stroud et al. | 2005/0031547 A1 | 2/2005 | Tamarkin et al. |
| 6,251,369 | B1 | 6/2001 | Stoltz | 2005/0042182 A1 | 2/2005 | Arkin |
| 6,258,374 | B1 | 7/2001 | Friess et al. | 2005/0054991 A1 | 3/2005 | Tobyn et al. |
| 6,271,295 | B1 | 8/2001 | Powell | 2005/0069566 A1 | 3/2005 | Tamarkin et al. |
| 6,287,546 | B1 | 9/2001 | Reich et al. | 2005/0074414 A1 | 4/2005 | Tamarkin et al. |
| 6,294,550 | B1 | 9/2001 | Place | 2005/0075407 A1 | 4/2005 | Tamarkin et al. |
| 6,299,900 | B1 | 10/2001 | Reed et al. | 2005/0079139 A1 | 4/2005 | Jacques et al. |
| 6,306,841 | B1 | 10/2001 | Place | 2005/0106197 A1 | 5/2005 | Blin et al. |
| 6,328,950 | B1 | 12/2001 | Franzke et al. | 2005/0186142 A1 | 8/2005 | Tamarkin et al. |
| 6,333,362 | B1 | 12/2001 | Lorant | 2005/0186147 A1 | 8/2005 | Tamarkin et al. |
| 6,358,541 | B1 | 3/2002 | Goodman | 2005/0196414 A1 | 9/2005 | Dake et al. |
| 6,372,234 | B1 | 4/2002 | Deckers et al. | 2005/0205086 A1 | 9/2005 | Tamarkin et al. |
| 6,383,471 | B1 | 5/2002 | Chen et al. | 2005/0232869 A1 | 10/2005 | Tamarkin et al. |
| 6,395,300 | B1 | 5/2002 | Straub et al. | 2005/0244342 A1 | 11/2005 | Friedman et al. |
| 6,403,069 | B1 | 6/2002 | Chopra et al. | 2005/0255048 A1 | 11/2005 | Hirsh et al. |
| 6,410,036 | B1 | 6/2002 | De Rosa et al. | 2005/0266035 A1 | 12/2005 | Healy et al. |
| 6,423,323 | B2 | 7/2002 | Neubourg | 2005/0271596 A1 | 12/2005 | Friedman et al. |
| 6,428,772 | B1 | 8/2002 | Singh et al. | 2005/0271598 A1 | 12/2005 | Friedman et al. |
| 6,433,033 | B1 | 8/2002 | Isobe et al. | 2005/0276836 A1 | 12/2005 | Wilson et al. |
| 6,437,006 | B1 | 8/2002 | Yoon | 2005/0281755 A1 | 12/2005 | Zarif et al. |
| 6,468,989 | B1 | 10/2002 | Chang et al. | 2005/0285912 A1 | 12/2005 | Delametter et al. |
| 6,524,594 | B1 | 2/2003 | Santora et al. | 2005/0287081 A1 | 12/2005 | Aust et al. |
| 6,531,118 | B1 | 3/2003 | Gonzalez et al. | 2006/0018937 A1 | 1/2006 | Friedman |
| 6,536,629 | B2 | 3/2003 | van der Heijden | 2006/0018938 A1 | 1/2006 | Neubourg |
| 6,544,530 | B1 | 4/2003 | Friedman | 2006/0029565 A1 | 2/2006 | Xu et al. |
| 6,548,074 | B1 | 4/2003 | Mohammadi | 2006/0057168 A1 | 3/2006 | Larm |
| 6,582,710 | B2 | 6/2003 | Deckers et al. | 2006/0088561 A1 | 4/2006 | Eini et al. |
| 6,596,287 | B2 | 7/2003 | Deckers et al. | 2006/0140984 A1 | 6/2006 | Tamarkin et al. |
| 6,599,513 | B2 | 7/2003 | Deckers et al. | 2006/0193789 A1 | 8/2006 | Tamarkin et al. |
| 6,620,773 | B1 | 9/2003 | Stork et al. | 2006/0222675 A1 | 10/2006 | Sabnis et al. |
| 6,649,571 | B1 | 11/2003 | Morgan | 2006/0233721 A1 | 10/2006 | Tamarkin et al. |

| Pub. No. | Date | Name |
|---|---|---|
| 2006/0254597 A1 | 11/2006 | Thompson |
| 2006/0269485 A1 | 11/2006 | Friedman et al. |
| 2006/0272199 A1 | 12/2006 | Licciardello et al. |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2007/0020213 A1 | 1/2007 | Tamarkin et al. |
| 2007/0020304 A1 | 1/2007 | Tamarkin et al. |
| 2007/0059253 A1 | 3/2007 | Popp et al. |
| 2007/0069046 A1 | 3/2007 | Eini et al. |
| 2007/0098647 A1 | 5/2007 | Neubourg |
| 2007/0148112 A1 | 6/2007 | Dingley et al. |
| 2007/0154402 A1 | 7/2007 | Trumbore et al. |
| 2007/0253911 A1 | 11/2007 | Tamarkin et al. |
| 2007/0280891 A1 | 12/2007 | Tamarkin et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0058055 A1 | 3/2008 | LeMay et al. |
| 2008/0069779 A1 | 3/2008 | Tamarkin et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0166303 A1 | 7/2008 | Tamarkin et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0253973 A1 | 10/2008 | Tamarkin et al. |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0317679 A1 | 12/2008 | Tamarkin et al. |
| 2009/0041680 A1 | 2/2009 | Tamarkin et al. |
| 2009/0068118 A1 | 3/2009 | Eini et al. |
| 2009/0130029 A1 | 5/2009 | Tamarkin et al. |
| 2009/0175799 A1 | 7/2009 | Tamarkin et al. |
| 2009/0180970 A1 | 7/2009 | Tamarkin et al. |

FOREIGN PATENT DOCUMENTS

| | | |
|---|---|---|
| DE | 10138495 | 2/2003 |
| DE | 102004016710 | 10/2005 |
| EP | 0156507 A1 | 10/1985 |
| EP | 0186453 | 7/1986 |
| EP | 211550 | 2/1987 |
| EP | 0270316 | 6/1988 |
| EP | 297436 | 1/1989 |
| EP | 414920 | 3/1991 |
| EP | 0488089 A1 | 6/1992 |
| EP | 0535327 | 4/1993 |
| EP | 0598412 | 11/1993 |
| EP | 0676198 | 10/1995 |
| EP | 0738516 | 10/1996 |
| EP | 0824911 | 2/1998 |
| EP | 0979654 | 2/2000 |
| EP | 1055425 A2 | 11/2000 |
| EP | 1287813 | 3/2003 |
| EP | 1 428 521 | 6/2004 |
| EP | 1428521 | 6/2004 |
| EP | 1189579 | 9/2004 |
| EP | 1475381 | 11/2004 |
| EP | 1500385 | 1/2005 |
| EP | 1758547 | 3/2007 |
| EP | 1584324 | 11/2007 |
| FR | 2774595 | 8/1999 |
| FR | 2915891 | 11/2008 |
| GB | 808104 | 1/1959 |
| GB | 808105 | 1/1959 |
| GB | 922930 | 4/1963 |
| GB | 1026831 | 4/1966 |
| GB | 1121358 | * 10/1966 |
| GB | 1376649 | 12/1974 |
| GB | 1397285 | 6/1975 |
| GB | 2114580 | 8/1983 |
| GB | 2166651 | 5/1996 |
| GB | 2337461 | 11/1999 |
| IL | 0152486 A0 | 5/2003 |
| JP | 02184614 | 7/1990 |
| JP | 2184614 | 7/1990 |
| JP | 2255890 | 10/1990 |
| JP | 5070340 | 3/1993 |
| JP | 5213734 | 8/1993 |
| JP | 6100414 | 4/1994 |
| JP | 6329532 | 11/1994 |
| JP | 7215835 | 8/1995 |
| JP | 2008040899 | 2/1996 |
| JP | 8119831 | 5/1996 |
| JP | 8165218 | 6/1996 |
| JP | 9099553 | 4/1997 |
| JP | 9110636 | 4/1997 |
| JP | 11250543 | 9/1999 |
| JP | 2000017174 | 1/2000 |
| JP | 2000080017 | 3/2000 |
| JP | 2000128734 | 5/2000 |
| JP | 2000191429 | 7/2000 |
| JP | 2000351726 | 12/2000 |
| JP | 2001019606 | 1/2001 |
| JP | 2002012513 | 1/2002 |
| JP | 2002047136 | 2/2002 |
| JP | 2003055146 | 2/2003 |
| JP | 2005350378 | 12/2005 |
| JP | 2006008574 | 1/2006 |
| JP | 2007131539 | 5/2007 |
| UA | 66796 | 6/2004 |
| WO | WO-86/05389 | 9/1986 |
| WO | WO-88/01863 | 3/1988 |
| WO | WO-89/06537 | 7/1989 |
| WO | WO-90/05774 | 5/1990 |
| WO | WO-92/00077 | 6/1991 |
| WO | WO-91/11991 | 8/1991 |
| WO | WO-92/11839 | 7/1992 |
| WO | WO-96/03115 | 2/1996 |
| WO | WO-96/19921 | 7/1996 |
| WO | WO-96/24325 | 8/1996 |
| WO | WO-96/27376 | 9/1996 |
| WO | WO-96/39119 | 12/1996 |
| WO | WO-97/39745 | 10/1997 |
| WO | WO-98/18472 | 5/1998 |
| WO | WO98/19654 | 5/1998 |
| WO | WO-98/21955 | 5/1998 |
| WO | WO-98/23291 | 6/1998 |
| WO | WO-98/36733 | 8/1998 |
| WO | WO-99/08649 | 2/1999 |
| WO | WO-99/20250 | 4/1999 |
| WO | WO-99/37282 | 7/1999 |
| WO | WO-00/09082 | 2/2000 |
| WO | WO-00/15193 | 3/2000 |
| WO | WO-00/61076 | 10/2000 |
| WO | WO-00/76461 | 12/2000 |
| WO | WO-01/08681 | 2/2001 |
| WO | WO-01/54679 | 8/2001 |
| WO | WO-01/70242 A2 | 9/2001 |
| WO | WO 01/82880 | 11/2001 |
| WO | WO-02/00820 | 1/2002 |
| WO | WO-02/28435 | 4/2002 |
| WO | WO-02/41847 A1 | 5/2002 |
| WO | WO-02/43490 | 6/2002 |
| WO | WO-02/062324 | 8/2002 |
| WO | WO-03/000223 | 1/2003 |
| WO | WO-03/051294 | 6/2003 |
| WO | WO-03/053292 | 7/2003 |
| WO | WO-03/055445 | 7/2003 |

| | | |
|---|---|---|
| WO | WO-03/075851 | 9/2003 |
| WO | WO-03/092641 | 11/2003 |
| WO | WO-2004/037225 | 5/2004 |
| WO | WO-2004/064833 | 8/2004 |
| WO | WO-2004/071479 A1 | 8/2004 |
| WO | WO-2004/078896 | 9/2004 |
| WO | WO-2004/112780 | 12/2004 |
| WO | WO-2005/011567 A2 | 2/2005 |
| WO | WO-2005/018530 A2 | 3/2005 |
| WO | WO-2005/032522 | 4/2005 |
| WO | WO-2005/044219 | 5/2005 |
| WO | WO-2005/065652 | 7/2005 |
| WO | WO-2005/076697 | 8/2005 |
| WO | WO-2005/097068 | 10/2005 |
| WO | WO-2005/097068 A1 | 10/2005 |
| WO | WO-2005/102539 | 11/2005 |
| WO | WO-2005/117813 | 12/2005 |
| WO | WO2006 003481 | 1/2006 |
| WO | WO-2006/003481 A2 | 1/2006 |
| WO | WO-2006/010589 | 2/2006 |
| WO | WO-2006/031271 | 3/2006 |
| WO | WO-2006/091229 | 8/2006 |
| WO | WO-2006/100485 | 9/2006 |
| WO | WO-2006/020682 | 11/2006 |
| WO | WO-2006/120682 | 11/2006 |
| WO | WO-2006/129161 | 12/2006 |
| WO | WO-2006/131784 | 12/2006 |
| WO | WO-2007/007208 | 1/2007 |
| WO | WO-2007/012977 | 2/2007 |
| WO | WO-2007/023396 | 3/2007 |
| WO | WO-2007/039825 | 4/2007 |
| WO | WO-2007/050543 | 5/2007 |
| WO | WO-2007/054818 | 5/2007 |
| WO | WO-2007/072216 | 6/2007 |
| WO | WO-2007/085899 | 8/2007 |
| WO | WO-2007/085902 | 8/2007 |
| WO | WO-2007/099396 | 9/2007 |
| WO | WO-2008/008397 | 1/2008 |
| WO | WO-2008/038147 | 4/2008 |
| WO | WO-2008/075207 | 6/2008 |
| WO | WO-2008/087148 | 7/2008 |

OTHER PUBLICATIONS

Barry, B.W. et al, Comparative bio-availability and activity of proprietary topical corticosteroid preparations: vasoconstrictor assays on thirty-one ointments, British Journal of Dermatology, 93, 563-571, 1975.

Martindale, The extra pharmacopoeia [28th] edition, Eds.: Reynolds, J.E.F. and Prasad, A.B., The Pharmaceutical Press, London, pp. 862-864, 1982.

Wormser et al., Protective effect of povidone-iodine ointment against skin lesions induced by sulphur and nitrogen mustards and by nonmustard vesicants, Arch. Toxicol., 1997, 71, 165-170.

Wormser, Early topical treatment with providone-iodine ointment reduces, and sometimes prevents, skin damage following heat stimulus, Letter to the Editor, Burns 24, pp. 383, 1998.

International Search Report, Foamix Ltd, International Application No. PCT/IB2006/003628, Jul. 12, 2007, 6 pages.

Molan, Peter Clark, "World Wide Wounds," Dec. 2001, 13 pages.

Office Action for U.S. Appl. No. 11/430,437, Tamarkin et al., May 9, 2008, 26 pages.

Final Office Action for U.S. Appl. No. 11/430,437, Tamarkin et al., Dec. 16, 2008, 18 pages.

Material Safety Data Sheet, Science Lab.com, Polyethylene Glycol 1000, MSDS, Nov. 6, 2008, 6 pages.

D.W.A. Sharp Dictionary of Chemistry, Penguin Books, 1983, 3 pages.

Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.

Material Safety Data Sheet, Progesterone, Apr. 26, 2006, 5 pages.

"Licking Vaginal Dryness Without a Prescription," Estronaut, Dec. 14, 2008, 3 pages.

Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.

Gill, A.M, et al., "Adverse Drug Reactions in a Paediatric Intensive Care Unit," Acta Paediatr 84:438-441, 1995.

Gschnait, F., et al., "Topical Indomethacin Protects from UVB and UVA Irriadiation," Arch. Dermatol. Res. 276:131-132, 1984.

Hall, Karla, "Diaper Area Hemangiomas: A Unique Set of Concerns," http://members.tripod.com/~Michelle_G/diaper.html, Dec. 1, 2008, 8 pages.

Skin Biology, CP Serum—Copper-Peptide Serum for Skin Regeneration and Reducing Wrinkles, Skin Biology, http;//web.archive.org/web/20030810230608/http://www.skinbio.com/cpserum.html, Dec. 1, 2008, 21 pages.

Galligan, John et al., "Adhesive Polyurethane Liners for Anterior Restorations," J. Dent. Res., Jul.-Aug. 1968, pp. 629-632.

Fonatana, Anthony J., "Water Activity: Why It is Important for Food Safety," International Conference on Food Safety, Nov. 16-18, 1998, pp. 177-185.

Ambrose, Ursula et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, vol. 35, No. 9, pp. 1799-1803, 1991.

Tan et al., "Effect of Carbopol and Polyvinlpyrrolidone on the Mechanical Rheological and Release Properties of Bioadhesive Polyethylene Glycol Gels," AAPS PharmSciTech, 2000; 1(3) Article 24, 2000, 10 pages.

Koerber S., "Humectants and Water Activity,", Water Activity News, Issue No. 1083-3943, 2000, 8 pages.

Third Party Submission for U.S. Appl. No. 12/014,088, Feb. 4, 2009, 4 pages.

European Official Action, European Patent Application No. 06831721.3, Feb. 3, 2009, 9 pages.

Alcohol SDA 40B.http://www.pharmco-prod.com/pages/MSDS/SDA_40B_200.pdf Accessed Dec. 9, 2008, 2 pages.

Arisan, http://www.arisankimya.com/kozmetik.htm Accessed Dec. 10, 2008.

Benet, et al., App-lication of NMR for the Determination of HLB Values of Nonionic Surfactants, Journal of the American Oil Chemists Society, vol. 49, 1972, 499-500.

Carbowax 1000MSDS; http://www.sciencelab.com/xMSDS-Polyethylene_glycol_1000-9926622. Accessed Dec. 13, 2008, 6 pages.

Cheshire, et al., Disorders of Sweating, www.medscape.com, Semin Neurol 23(4):399-406, 2003.

Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.

Dalby, "Determination of Drug Solubility in Aerosol Propellants," Pharmaceutical Research, vol. 8, No. 9, 1991, pp. 1206-1209.

Denatonium Benzoate http://www.newdruginfo.com/pharmaceopeia/usp28/v28230/usp28nf23s0_m22790.htm Accessed Dec. 9, 2008.

Eini, M. et al., Apparatus and Method for Releasing a Measured Amount of Content from a Container, filed Apr. 18, 2006, U.S. Appl. No. 11/406,133.

Ethanol, Accessed http://www.sigmaaldrich.com/catalog/ProductDetail.do?N4=E7023SIAL& N5=SEARCH_CONCAT_PNOBRAND_KEY&F=SPEC Dec. 9, 2008, 2 pages.

European Patent Application No. 06831721, Official Action, Feb. 3, 2009, 9 pages.

Flick, Cosmetic and Toiletry Formulations, vol. 5, 2nd Edition, Copyright 1996.

Friedman, D. et al., Polypropyle NE Glycol Foamable Vehicle and Pharmaceutical Compositions Thereof, filed Jun. 7, 2007, U.S. Appl. No. 11/811,140.

Friedman. et al., Antibiotic Kit and Composition Uses Thereof, filed Jun. 7, 2006, U.S. Appl. No. 11/448,490.

Gill, A.M, et al., "Adverse Drug Reactions in a Paediatric Intensitve Care Unit," Acta Paediatr 84:438-441, 1995.

Glaser, et al., Hyperhidrosis: A Comprehensive and Practical Approach to Patient Management, Expert Rev. Dermatol. 1(6), 773-775 (2006).

Hall, Karla, "Diaper Area Hemanglomas: A Unique Set of Concerns," http://members.tripod.com/~Michelle_G/diaper.html, Dec. 1, 2008, 8 pages.

Hill, Randall M. (Ed.) Silicone Surfactants, Table of Contents and Chapter 7, "Silicone Surfactants: Applicants in the Personal Care Industry," by David T. Floyd (30 Pages).

Hydroxyethylcelllulose. htt;://terpconnect.umd.edu/~choi/MSDS/Sigma-Aldrich/HYDROXYETHYL%20CELLULOSE, 5 pages.

Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.

International Search Report and Written Opinion, International Application No. PCT/IB2006/003628, Foamix Ltd., Dec. 7, 2007, 15 pages.

Kalkan, et al., The Measurement of Sweat Intensity Using a New Technique, Tr. J. of Medical Sciences 28, 515-517 (1998).

Kathon™ CG (product information sheet by Rohm and Haas, Jun. 2006).

Kinnunen, Contact Dermatitis Sep. 1989; 21(3): 154-8.

Koerber, S., "Humectants and Water Activity," Water Activity News, 2000, ISSN No. 1083-3943.

Licking Vaginal Dryness without a Prescription. Accessed http://www.estronaut.com/a/vag_dryness.htm on Dec. 14, 2008.

Merriam-Webster Online Dictionaary, 2008, "Mousse," Merriam-Webster Online, Dec. 8, 2008 http://www.merriam-webster.com/dictionary/mousse.

Metronidazole. www.usp.org/pdf/EN/veterinary/metronidazole.pdf. accessed Sep. 10, 2009, 4 pages.

Office Action received from the U.S. Patent Office for U.S. Appl. No. 11/430,437, May 9, 2008, 55 pages.

Office Action received from the U.S. Patent Office, U.S. Appl. No. 11/430,599, Jul. 28, 2008, 58 pages.

Pendergrass, Gynecol Obstet. Invest. 1996:42(3):178-82.

Progesterone MSDS. http://www.usp.org.pdf.EN/referenceStandards/msds/1568007.pdf on Dec. 14, 2002, 5 pages.

Scott as Published in Pharmaceutical Dosage Forms; Disperse Systems, vol. 3, Copyright 1998.

Sigma-Aldrich, Material Safety Data Sheet, Hydroxyethyl Cellulose, Mar. 3, 2004, 5 pages.

Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008.

Emulsifiers with HLB values. http://www.theherbarie.com/files/resources-center/formulating/Emulsifiers_HLB_Values.pdf accessed Aug. 5, 2009 (3 pps).

Hashim, et al. "Tinea versicolor and visceral leishmaniasis," Int J Dermatol., Apr. 1994; 33(4), pp. 258-259 (abstract only).

Hepburn, NC., "Cutaneous leishmaniasis," Clin Exp Dermatol, Jul. 2000; 25(5), pp. 363-370 (abstract only).

OM Cinnamate. http://www.makingcosmetics.com/sunscreens/OM-Cinnamate-p102.html accessed Sep. 26, 2009.

Savin, et al., "Tinea versicolor treated with terbinafine 1% solution," Int J. Dermatol, Nov. 1999; 38(11), pp. 863-865.

Schmidt A., "Malassezia furfur: a fungus belonging to the physiological skin flora and its relevance in skin disorders," Curtis., Jan. 1997; 59(1), pp. 21-24 (abstract).

Shear, et al., "Pharmacoeconomic analysis of topical treatments for tinea infections," Pharmacoeconomics. Mar. 1995; 7(3); pp. 251-267 (abstract only).

Sigma Aldrich, "HLB-Numbers in Lithography Nanopatterning," http://www.sigmaaldrich.com/materials-science/micro-and-nanoelectronics/lithography-nanopatterning/hlb-numbers.html, accessed: Feb. 2, 2009, pp. 1-3.

Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat. Jun. 2002;13(2):51-60 (abstract only).

Torres-Rodriguez, JM., "New topical antifungal drugs," Arch Med Res. 1993 Winter; 24(4), pp. 371-375 (abstract).

* cited by examiner

Candida albicans
*Composition A effective*
*Compositions B and C ineffective*

Trichophyton rubrum
*Compositions A, B and C effective*

Trichophyton mentagrophytes
Compositions A and B effective
Composition C ineffective

Microsporum canis
*Composition A and B effective*
*Composition C ineffective*

FIG. 1D

FOAMABLE VEHICLE AND PHARMACEUTICAL COMPOSITIONS THEREOF

CROSS REFERENCE TO RELATED APPLICATIONS

This application is a continuation-in-part application of co-pending U.S. patent application Ser. No. 10/835,505, filed on Apr. 28, 2004, which claims the benefit of priority under 35 U.S.C. §119(e) to U.S. patent application Ser. No. 60/530,015, filed on Dec. 16, 2003, and U.S. patent application Ser. No. 60/492,385, filed on Aug. 4, 2003, all entitled "Oleaginous Pharmaceutical Foam" and all hereby incorporated in their entirety by reference.

This application claims the benefit under 35 U.S.C. §119 (e) of U.S. Provisional Patent Application No. 60/679,020, filed on May 9, 2005, entitled Hygroscopic Anti-Infective Compositions, which is herein incorporated by reference in its entirety.

This application claims the benefit under 35 U.S.C. §119 (e) of U.S. Provisional Patent Application No. 60/784,793, filed on Mar. 21, 2006, entitled Polyol Foamable Vehicle and Pharmaceutical Compositions Thereof, which is herein incorporated by reference in its entirety.

BACKGROUND OF THE INVENTION

This invention relates to foamable pharmaceutical and cosmetic compositions.

External topical administration is an important route for the administration of drugs in disease treatment. Many groups of drugs, including, for example, antibiotic, anti-fungal, anti-inflammatory, anesthetic, analgesic, anti-allergic, corticosteroid, retinoid and anti-proliferative medications are preferably administered in hydrophobic media, namely ointment. However, ointments often form an impermeable barrier, so that metabolic products and excreta from the wounds to which they are applied are not easily removed or drained away. Furthermore, it is difficult for the active drug dissolved in the carrier to pass through the white petrolatum barrier layer into the wound tissue, so the efficacy of the drug is reduced. In addition, ointments and creams often do not create an environment for promoting respiration of the wound tissue and it is not favorable to the normal respiration of the skin. An additional disadvantage of petroleum jelly-based products relates to the greasy feeling left following their topical application onto the skin, mucosal membranes and wounds.

Foams and, in particular, foams that are substantially based on non-aqueous solvents are complicated systems which do not form under all circumstances. U.S. patent application Ser. No. 20050031547 relates to stable oleaginous cosmetic or therapeutic foam compositions containing certain active agents, having unique therapeutic properties and methods of treatment using such compositions. The foamable carrier includes at least one solvent selected from a hydrophobic solvent, a silicone oil, an emollient, a co-solvent, and mixtures thereof, wherein the solvent is present at a concentration of about 70% to about 96.5% by weight of the total composition, at least a non-ionic surface-active agent at a concentration of about 0.1% to less than about 10% by weight of the total composition; at least one gelling agent at a concentration of about 0.1% to about 5% by weight of the total composition; a therapeutically effective amount of at least one active agent; and at least one liquefied or compressed gas propellant, at a concentration of about 3% to about 25% by weight of the total composition.

WO 00/09082 teaches an anhydrous cleansing composition for topical application to human skin, comprising an ionic surfactant, glycerine, propylene glycol and water insoluble benefit agents. According to the examples of WO 00/09082, the concentration of the ionic surfactant is in the range of 18-22%.

U.S. Pat. No. 6,765,001 comprises a composition, method of enhancing potency and method of delivering corticosteroids in a vehicle comprising two or more penetration enhancers selected from the group consisting of diisopropyl adipate, dimethyl isosorbide, propylene glycol, 1,2,6-hexapetriol, and benzyl alcohol; and one or more of the group consisting of solvents and emulsifiers.

WO91/11991 teaches an essentially non-aqueous and non-oily foamable composition, that can be used for rectal administration of pharmaceuticals, comprising a liquid polar polyol or polyol mixture, a pharmaceutically active ingredient and at least one foam stabilizing and emulsifying surfactant. However, this foam composition is associated with disadvantages and the purposes of the present invention are not attained (see comparative example below).

There remains an unmet need for improved, easy to use, stable and non-irritating anti-infective foam formulations, intended for treatment of dermal and mucosal tissues. Particularly, there remains an unmet need for improved, easy to use, stable and non-irritating anti-infective foam formulations, with unique therapeutic properties.

SUMMARY OF THE INVENTION

In one aspect, the invention provides a hygroscopic pharmaceutical composition including at least one hygroscopic substance at a sufficient concentration to provide an Aw value of the hygroscopic pharmaceutical composition of less than 0.9 and an anti-infective agent; or the Aw value is in the range of about 0.8 and about 0.9; (2) about 0.7 and about 0.8; and (3) less than about 0.7

In one or more embodiments, the hygroscopic pharmaceutical composition further includes at least one component, selected from the group consisting of about 0.01% to about 5% by weight of at least one polymeric agent selected from a bioadhesive agent, a gelling agent, a film forming agent and a phase change agent; and about 0.2% to about 5% by weight of a surface-active agent.

In one or more embodiments, the hygroscopic substance is selected from the group consisting of polyethylene glycols (PEGs), surfactants comprising PEG, polyols, monosaccharides, disaccharides, oligosaccharides and sugar alcohols in an amount to provide hygroscopic properties, and honey.

In another aspect, the invention provides a foamble pharmaceutical carrier including about 50% to about 98% of a polar solvent selected from the group consisting of (1) a polyol and (2) a polyethylene glycol (PEG); 0% to about 48% of a secondary polar solvent; about 0.2% to about 5% by weight of a surface-active agent; about 0.01% to about 5% by weight of at least one polymeric agent; and a liquefied or compressed gas propellant at a concentration of about 3% to about 25% by weight of the total composition.

In one or more embodiments, the compositions further comprise up to 10% of water.

In one or more embodiments, the composition is substantially non-aqueous and/or substantially alcohol-free.

In one or more embodiments, the composition further comprises a therapeutically effective concentration of one or more active agents.

In one or more embodiments, the polyol is selected from the group consisting of a diol, a triol and a saccharide, and the triol may be selected from the group consisting of glycerin, butane-1,2,3-triol, butane-1,2,4-triol and hexane-1,2,6-triol, or the diol is selected from the group consisting of propylene glycol, butanediol, butenediol, butynediol, pentanediol, hexanediol, octanediol, neopentyl glycol, 2-methyl-1,3-propanediol, diethylene glycol, triethylene glycol, tetraethylene glycol, dipropylene glycol and dibutylene glycol.

In one or more embodiments, the polyol consists of at least one diol and at least one triol, and wherein the ratio between the diol and triol is between 9:1 and 1:1.

In one or more embodiments, the composition includes a mixture of at least one polyol and at least one PEG, and the PEG may be selected from the group consisting of PEG 200, PEG 300, PEG 400, PEG 600, PEG 1000, PEG 4000, PEG 6000 and PEG 8000, or the composition contains one or more PEGs in a concentration to provide viscosity of less than 12,000 CPs.

In one or more embodiments, the composition includes a secondary polar solvent selected from the group consisting of dimethyl isosorbide, tetrahydrofurfuryl alcohol polyethyleneglycol, ether, DMSO, a pyrrolidone, N-Methyl-2-pyrrolidone, 1-Methyl-2-pyrrolidinone, ethyl proxitol, dimethylacetamide, a PEG-type surfactant, an alpha hydroxy acid, lactic acid and glycolic acid, or the secondary polar solvent is dimethyl isosorbide.

In one or more embodiments, the composition includes (1), at least one polar solvent selected from a diol, a triol and PEG, and (2) at least one secondary polar solvent, and for example, the polar solvent comprises a mixture of at least one polyol and at least one PEG, and for example, the polyol comprises a mixture of at least two polyols.

In one or more embodiments, the ratio between the polyol and/or PEG and the secondary polar solvent is between 9:1 and 1:1.

In another aspect of the inventin, a method of treating a disorder of mammalian subject includes administering a foamable therapeutic composition to a target area, the composition comprising a therapeutically effective concentration of an active agent, about 50% to about 98% of a polar solvent selected from the group consisting of (1) a polyol; and (2) a polyethylene glycol; 0% to about 48% of a secondary polar solvent; about 0.2% to about 5% by weight of a surface-active agent; about 0.01% to about 5% by weight of at least one polymeric agent; and a liquefied or compressed gas propellant at a concentration of about 3% to about 25% by weight of the total composition.

In one or more embodiments, the target site is selected from the group consisting of the skin, a body cavity, a mucosal surface, the nose, the mouth, the eye, the ear canal, the respiratory system, the vagina and the rectum.

BRIEF DESCRIPTION OF THE DRAWINGS

Various objects, features, and advantages of the present invention can be more fully appreciated with reference to the following detailed description of the invention when considered in connection with the following drawings, in which like reference numerals identify like elements. The following drawings are for the purpose of illustration only and are not intended to be limiting of the invention, the scope of which is set forth in the claims that follow.

DETAILED DESCRIPTION OF THE INVENTION

Figure 1A:
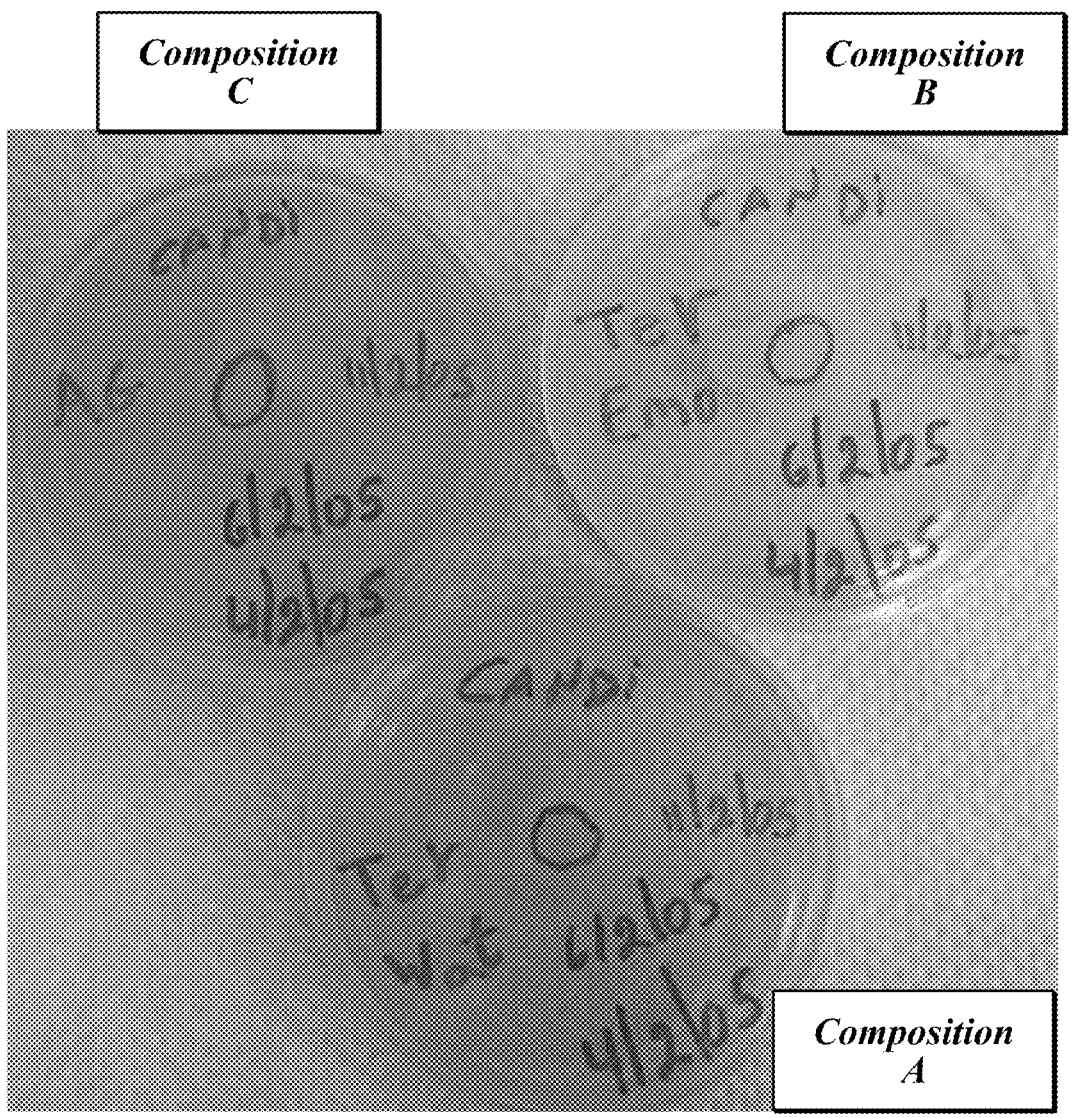
FIG. 1A-D illustrates the in vitro effect of effect of Composition A, consisting of 2% terbinafine, 95.3% gr. polyethylene glycol, 0.5% hydroxypropyl cellulose and 2.2% steareth-2, in comparison with Composition B (an oil in water emulsion containing 2% terbinafine) and Composition C a commercial 1% bifonazole cream, in the treatment of three fungal strains (*microsporum canis, trichophyton mentagrophytes* and *trichophyton rubrum*) and one yeast (*candida albicans*).
Figure 1B:
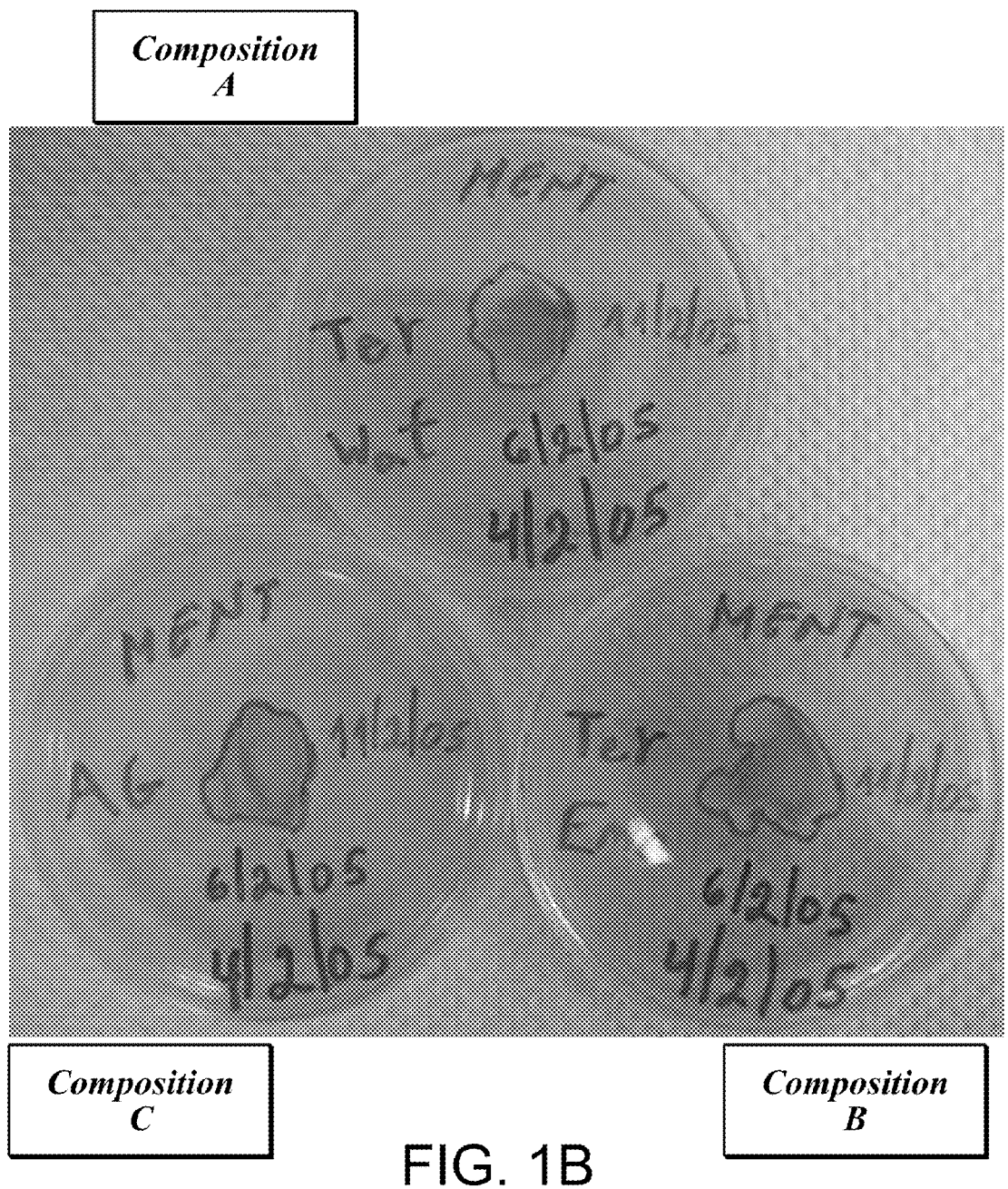

The present invention relates to a composition for use as foamable vehicle composition.

According to one or more embodiments of the present invention, the foamable carrier, includes:
 a. about 50% to about 98% of a polar solvent selected from the group consisting of (1) a polyol; and (2) a polyethylene glycol;
 b. 0% to about 48% of a secondary polar solvent;
 c. about 0.2% to about 5% by weight of a surface-active agent;
 d. about 0.01% to about 5% by weight of at least one polymeric agent; and
 e. a liquefied or compressed gas propellant at a concentration of about 3% to about 25% by weight of the total composition.

All % values are provided on a weight (w/w) basis.

Water, up to 25% of the composition, and more preferably up to 10%, and optional ingredients are added to complete the total mass to 100%. In certain cases, the composition contains two active agents that require different pH environments in order to remain stable. For example, corticosteroids are typically stable at acidic pH (they have a maximum stability at a pH of about 4-6) and vitamin D analogues are typically stable at basic pH (they have a maximum stability at pH values above about 8). In other cases, the active agent degrades in the presence of water, and therefore, in such cases the present of water in the composition is not desirable. Thus, in certain preferred embodiments, the composition is substantially non-aqueous. The term "substantially non-aqueous" is intended to indicate that the composition has a water content below about 5%, preferably below about 2%, such as below about 1.5%.

Upon release from an aerosol container, the foamable carrier forms an expanded foam suitable for the treatment of an infected surface and for topical administration to the skin, a body surface, a body cavity or a mucosal surface.

The identification of a "polar solvent", as used herein, is not intended to characterize the solubilization capabilities of the solvent for any specific active agent or any other component of the foamable composition. Rather, such information is provided to aid in the identification of materials suitable for use as a part in the foamable compositions described herein.

Polyol

In an embodiment of the present invention, the polar solvent is a polyol. A polyol is an organic substance that contains at least two hydroxy groups in its molecular structure.

In one or more embodiments, the foamable carrier contains at least one diol (a compound that contains two hydroxy groups in its molecular structure). Examples of diols include propylene glycol (e.g., 1,2-propylene glycol and 1,3-propylene glycol), butanediol (e.g., 1,2-butanediol, 1,3-butanediol, 2,3-butanediol and 1,4-butanediol), butanediol (e.g., 1,3-butanediol and 1,4-butenediol), butynediol, pentanediol (e.g., pentane-1,2-diol, pentane-1,3-diol, pentane-1,4-diol, pentane-1,5-diol, pentane-2,3-diol and pentane-2,4-diol), hexanediol (e.g., hexane-1,6-diol hexane-2,3-diol and hexane-2, 56-diol), octanediol (e.g., 1,8-octanediol), neopentyl glycol, 2-methyl-1,3-propanediol, diethylene glycol, triethylene glycol, tetraethylene glycol, dipropylene glycol and dibutylene glycol.

In one or more embodiments, the foamable carrier contains at least one triol (a compound that contains three hydroxy groups in its molecular structure), such as glycerin, butane-1,2,3-triol, butane-1,2,4-triol and hexane-1,2,6-triol.

In one or more embodiments, the polyol is a mixture of polyols. In one or more embodiments, the mixture of polyols contains at least one diol and at least one triol. According to certain embodiments the ratio between the diol and triol is between 9:1 and 1:1.

In one or more embodiments, part of mixture of polyols is a saccharide. Exemplary saccharides include, but are not limited to monosaccharide, disaccharides, oligosaccharides and sugar alcohols.

A monosaccharide is a simple sugar that cannot be hydrolysed to smaller units. Empirical formula is $(CH2O)n$ and range in size from trioses (n=3) to heptoses (n=7). Exemplary monosaccharide compounds are ribose, glucose, fructose and galactose.

Disaccharides are made up of two monosaccharides joined together, such as sucrose, maltose and lactose.

A sugar alcohol (also known as a polyol, polyhydric alcohol, or polyalcohol) is a hydrogenated form of saccharide, whose carbonyl group (aldehyde or ketone, reducing sugar) has been reduced to a primary or secondary hydroxyl group. They are commonly used for replacing sucrose in foodstuffs, often in combination with high intensity artificial sweeteners to counter the low sweetness. Some exemplary sugar alcohols, which are suitable for use according to the present invention are mannitol, sorbitol, xylitol, maltitol, lactitol. (Maltitol and lactitol are not completely hydrogenated compounds—they are a monosaccharide combined with a polyhydric alcohol). Mixtures of polyols, including (1) at least one polyol selected from a diol and a triol; and (2) a saccharide are contemplated within the scope of the present invention.

Polyethylene Glycol

In an embodiment of the present invention, the polar solvent consists of a polymerized ethylene glycol, namely polyethylene glycol, which is also termed "PEG". Exemplary PEGs are provided in the following table.

| Composition | Av. Molecular weight | Appearance | Melting point (° C.) |
|---|---|---|---|
| PEG 200 | 190~210 | Oily liquid | |
| PEG 300 | 285~315 | Oily liquid | |
| PEG 400 | 380~420 | Oily liquid | |
| PEG 600 | 570~630 | Oily liquid | 17~22 |
| PEG 1000 | 950~1050 | Solid | 35~40 |
| PEG 4000 | 3800~4400 | Solid | 53~58 |
| PEG 6000 | 5600~6400 | Solid | 55~60 |
| PEG 8000 | 7500~8500 | Solid | 58~65 |

Thus, in an embodiment of the present invention, the PEG is selected from the group consisting of PEG 200, PEG 300, PEG 400, PEG 600, PEG 1000, PEG 4000, PEG 6000 and PEG 8000. The foamable carrier according to the present invention can contain a single PEG or a mixture of two or more PEGs. PEGs having molecular weight of more that about 1000 possess gelling properties; i.e., they increase the viscosity of a composition. Therefore, by combining PEGs with different molecular weights/melting points, one can attain varying levels of flowability as desirable for the treatment of a given target site. The concentration of the PEG should be in a level that results in viscosity, prior to filling of the composition into aerosol canisters, of less than 12,000 CPs, and more preferably, less than 10,000 CPs.

Secondary Polar Solvent

Optionally, a secondary polar solvent is added to the foamable composition of the present invention. The secondary polar solvent is selected from a variety of organic solvents that are typically miscible on both water and oil. Examples of polar solvent that can be contained in the foamable carrier of the present invention include dimethyl isosorbide, tetrahydrofurfuryl alcohol polyethyleneglycol ether (glycofurol), DMSO, pyrrolidones, (such as N-Methyl-2-pyrrolidone and 1-Methyl-2-pyrrolidinone), ethyl proxitol, dimethylacetamide (DMAc), PEG-type surfactants and alpha hydroxy acids, such as lactic acid and glycolic acid.

Solubilization and Penetration Enhancement

In many cases, polyols, PEGs and polar solvents possess a high solubilizing power and thus, they can enable increased concentrations of a pharmaceutical active agent. Polyols, PEGs and polar solvents are also known for their skin penetration enhancement properties. These properties enable high drug bioavailability in the target area of treatment, resulting in an enhanced therapeutic effect. Occasionally, combinations of a polyol, PEGs and a secondary polar solvent, exhibit an increased permeability across the skin, as suggested, for example, in Eur J Pharm Biopharm. November 1998;46(3):265-71.

Thus, in one or more embodiments, the foamable carrier contains (1) at least one polar solvent, selected from a polyol (selected from a diol and a triol) and PEG; and (2) at least one secondary polar solvent.

In one or more embodiments, the foamable carrier contains (1) a mixture of at least two polyols; and (2) at least one secondary polar solvent. In additional embodiments, the foamable carrier contains a mixture of at least one polyol and at least one PEG; yet in other embodiments the foamable carrier contains (1) a mixture of at least one polyol and at least one PEG and (2) at least one secondary polar solvent.

According to certain embodiments the ratio between the polyol and/or PEG and the secondary polar solvent is between 9:1 and 1:1.

In certain embodiments, the polyol is selected from the group consisting of propylene glycol, hexylene glycol and glycerin (and mixtures thereof); and the secondary polar solvent is selected from the group consisting of dimethyl isosorbide, diethylene glycol monoethyl ether, a liquid polyethylene glycol and glycofurol.

In certain embodiments, the foamable carrier contains (1) at least one polyol; and (2) dimethyl isosorbide.

Short chain alcohols, such as ethanol and propanol are known as polar solvents, however, according to one or more embodiments, the composition of the present invention is substantially alcohol-free, i.e., free of short chain alcohols. Short chain alcohols, having up to 5 carbon atoms in their carbon chain skeleton and one hydroxyl group, such as ethanol, propanol, isopropanol, butanol, iso-butanol, t-butanol and pentanol, are considered less desirable polar solvents due to their skin-irritating effect.

Thus, in certain embodiments, the composition is substantially alcohol-free and includes less than about 5% final concentration of lower alcohols, preferably less than about 2%, more preferably less than about 1%. However, in other embodiments, a short chain alcohol can be included in the composition, as long as the ratio between the short chain alcohol and the polyol is less than 1:4 by weight.

Polymeric Agent

The composition of the present invention contains a polymeric agent. It has been documented that the presence of a polymeric agent is necessary for the creation of foam, having fine bubble structure, which does not readily collapse upon release from the pressurized aerosol can. The polymeric agent serves to stabilize the foam composition and to control drug residence in the target organ. Preferably, the polymeric agent is soluble or readily dispersible in the polyol; or in the mixture of a polyol and an additional polar solvent.

Non-limiting examples of polymeric agents that are soluble or readily dispersible in propylene glycol are Hydroxypropylcellulose and carbomer (homopolymer of acrylic acid is crosslinked with an allyl ether pentaerythritol, an allyl ether of sucrose, or an allyl ether of propylene, such as Carbopol® 934, Carbopol® 940, Carbopo® 941, Carbopol® 980 and Carbopol® 981.

Other polymeric agents are suitable for use according to the present invention provided that they are soluble or readily dispersible in the polyol; or in the mixture of a polyol and an additional polar solvent, on a case by case basis.

Exemplary polymeric agents include, in a non-limiting manner, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, amine-bearing polymers such as chitosan; acidic polymers obtainable from natural sources, such as alginic acid and hyaluronic acid; chemically modified starches and the like, carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like.

Additional exemplary polymeric agents include semi-synthetic polymeric materials such as cellulose ethers, such as methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxyethylcellulose, and cationic celluloses. Polyethylene glycol, having molecular weight of 1000 or more (e.g., PEG 1,000, PEG 4,000, PEG 6,000 and PEG 10,000) also have gelling capacity and while they are considered herein as "secondary polar solvents", as detailed herein, they are also considered polymeric agents.

Mixtures of the above polymeric agents are contemplated.

The concentration of the polymeric agent should be selected so that the composition, after filling into aerosol canisters, is flowable, and can be shaken in the canister. In one or more embodiments, the concentration of the polymeric agent is selected such that the viscosity of the composition, prior to filling of the composition into aerosol canisters, is less than 12,000 CPs, and more preferably, less than 10,000 CPs.

Surface-active Agent

The composition of the present invention further contains a surface-active agent. Surface-active agents (also termed "surfactants") include any agent linking oil and water in the composition, in the form of emulsion. A surfactant's hydrophilicilipophilic balance (HLB) describes the emulsifier's affinity toward water or oil. HLB is defined for non-ionic surfactants. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average).

According to one or more embodiments the composition contains a single surface active agent having an HLB value between about 7 and 12, or more than one surface active agent and the weighted average of their HLB values is between about 7 and about 12.

Preferably, the composition of the present invention contains a non-ionic surfactant. Nonlimiting examples of possible non-ionic surfactants include polysorbates, such as polyoxyethylene (20) sorbitan monostearate (Tween 60) and poly(oxyethylene) (20) sorbitan monooleate (Tween 80); poly(oxyethylene) (POE) fatty acid esters, such as Myrj 45, Myrj 49, Myrj 52 and Myrj 59; poly(oxyethylene)alkylyl ethers, such as poly(oxyethylene)cetyl ether, poly(oxyethylene) palmityl ether, polyethylene oxide hexadecyl ether, polyethylene glycol cetyl ether, brij 38, brij 52, brij 56 and brij W1; sucrose esters, partial esters of sorbitol and its anhydrides, such as sorbitan monolaurate and sorbitan monolaurate; mono or diglycerides, isoceteth-20, and mono-, di- and tri-esters of sucrose with fatty acids (sucrose esters).

Non-limiting examples of non-ionic surfactants that have HLB of about 7 to about 12 include PEG 100 stearate (HLB=11), Laureth 4 (HLB=9.7) and cetomacrogol ether (e.g., polyethylene glycol 1000 monocetyl ether).

Yet, in additional embodiments, the composition contains a single surface active agent or a combination of surface active agents having an HLB values between about 9 and about 14; and in other embodiments, the composition contains one or more surface active agents, having an HLB value between about 2 and about 9.

In certain cases, the surface active agent is selected from the group of cationic, zwitterionic, amphoteric and ampholytic surfactants, such as sodium methyl cocoyl taurate, sodium methyl oleoyl taurate, sodium lauryl sulfate, triethanolamine lauryl sulfate and betaines.

In one or more embodiments of the present invention, the surface-active agent includes at least one non-ionic surfactant. Ionic surfactants are known to be irritants. Therefore, non-ionic surfactants are preferred in applications including sensitive tissue such as found in most mucosal tissues, especially when they are infected or inflamed. We have surprisingly found that non-ionic surfactants alone provide foams of excellent quality, i.e. a score of "E" according to the grading scale discussed herein below.

Thus, in a preferred embodiment, the surface active agent, the composition contains a non-ionic surfactant, or a mixture of non-ionic surfactants as the sole surface active agent. Yet, in additional embodiments, the foamable composition includes a mixture of at least one non-ionic surfactant and at least one ionic surfactant in a ratio in the range of about 100:1 to 6:1. In further embodiments, surface active agent comprises a combination of a non-ionic surfactant and an ionic surfactant, at a ratio of between 1:1 and 20:1. The concentration of the surface active agent is between about 0.1% and about 5%.

Hydrophobic Solvent

Optionally, the foamable carrier further contains at least one hydrophobic solvent. The identification of a "hydrophobic solvent", as used herein, is not intended to characterize the solubilization capabilities of the solvent for any specific active agent or any other component of the foamable composition. Rather, such information is provided to aid in the identification of materials suitable for use as a part in the foamable compositions described herein.

A "hydrophobic solvent" as used herein refers to a material having solubility in distilled water at ambient temperature of less than about 1 gm per 100 mL, more preferable less than about 0.5 gm per 100 mL, and most preferably less than about 0.1 gm per 100 mL.

In one or more embodiments, the hydrophobic organic carrier is an oil, such as mineral oil, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, unsaturated or polyunsaturated oils, such as olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils; essential oils; and silicone oils, such as dimethicone, cyclomethicone, polyalkyl siloxanes, polyaryl siloxanes, polyalkylaryl siloxanes and polyether siloxane copolymers, polydimethylsiloxanes(dimethicones) and poly(dimethylsiloxane)-(diphenyl-siloxane) copolymers.

Foam Adjuvant

Optionally, a foam adjuvant is included in the foamable carriers of the present invention to increase the foaming capacity of surfactants and/or to stabilize the foam. In one or more embodiments of the present invention, the foam adjuvant agent includes fatty alcohols having 15 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50). Fatty alcohols, derived from beeswax and including a mixture of alcohols, a majority of which has at least 20 carbon atoms in their carbon chain, are especially well suited as foam adjuvant agents. The amount of the fatty alcohol required to support the foam system is inversely related to the length of its carbon chains. Foam adjuvants, as defined herein are also useful in facilitating improved spreadability and absorption of the composition.

In one or more embodiments of the present invention, the foam adjuvant agent includes fatty acids having 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof. As for fatty alcohols, the amount of fatty acids required to support the foam system is inversely related to the length of its carbon chain.

Optionally, the carbon atom chain of the fatty alcohol or the fatty acid may have at least one double bond. A further class of foam adjuvant agent includes a branched fatty alcohol or fatty acid. The carbon chain of the fatty acid or fatty alcohol also can be substituted with a hydroxyl group, such as 12-hydroxy stearic acid.

Additional Components

In an embodiment of the present invention, a composition of the present invention includes one or more additional components. Such additional components include but are not limited to anti perspirants, anti-static agents, buffering agents, bulking agents, chelating agents, cleansers, colorants, conditioners, deodorants, diluents, dyes, emollients, fragrances, hair conditioners, humectants, pearlescent aids, perfuming agents, permeation enhancers, pH-adjusting agents, preservatives, protectants, skin penetration enhancers, softeners, solubilizers, sunscreens, sun blocking agents, sunless tanning agents, viscosity modifiers and vitamins. As is known to one skilled in the art, in some instances a specific additional component may have more than one activity, function or effect.

In an embodiment of the present invention, the additional component is a pH adjusting agent or a buffering agent. Suitable buffering agents include but are not limited to acetic acid, adipic acid, calcium hydroxide, citric acid, glycine, hydrochloric acid, lactic acid, magnesium aluminometasilicates, phosphoric acid, sodium carbonate, sodium citrate, sodium hydroxide, sorbic acid, succinic acid, tartaric acid, and derivatives, salts and mixtures thereof.

In an embodiment of the present invention, the additional component is an emollient. Suitable emollients include but are not limited to mineral oil, lanolin oil, coconut oil, cocoa butter, olive oil, aloe vera extract, jojoba oil, castor oil, fatty acids, fatty alcohols, diisopropyl adipate, hydroxybenzoate esters, benzoic acid esters of C9 to C15 alcohols, isononyl iso-nonanoate, silicone oils, polyethers, C12 to C15 alkyl benzoates, oleic acid, stearic fatty acid, cetyl alcohols, hexadecyl alcohol, dimethyl polysiloxane, polyoxypropylene cetyl ether, polyoxypropylene butyl ether, and derivatives, esters, salts and mixtures thereof.

In an embodiment of the present invention, the additional component is a humectant. Suitable humectants include but are not limited to guanidine, urea, glycolic acid, glycolate salts, ammonium glycolate, quaternary alkyl ammonium glycolate, lactic acid, lactate salts, ammonium lactate, quaternary alkyl ammonium lactate, aloe vera, aloe vera gel, allantoin, urazole, alkoxylated glucose, hyaluronic acid, lactamide monoethanolamine, acetamide monoethanolamine and derivatives, esters, salts and mixtures thereof.

In an embodiment of the present invention, the additional component is a preservative. Suitable preservatives include but are not limited to C12 to C15 alkyl benzoates, alkyl p-hydroxybenzoates, aloe vera extract, ascorbic acid, benzalkonium chloride, benzoic acid, benzoic acid esters of C9 to C15 alcohols, butylated hydroxytoluene, castor oil, cetyl alcohols, chlorocresol, citric acid, cocoa butter, coconut oil, diazolidinyl urea, diisopropyl adipate, dimethyl polysiloxane, DMDM hydantoin, ethanol, fatty acids, fatty alcohols, hexadecyl alcohol, hydroxybenzoate esters, iodopropynyl butylcarbamate, isononyl iso-nonanoate, jojoba oil, lanolin oil, methylparaben, mineral oil, oleic acid, olive oil, polyethers, polyoxypropylene butyl ether, polyoxypropylene cetyl ether, potassium sorbate, silicone oils, sodium propionate, sodium benzoate, sodium bisulfite, sorbic acid, stearic fatty acid, vitamin E, vitamin E acetate and derivatives, esters, salts and mixtures thereof.

In an embodiment of the present invention, the additional component is a skin penetration enhancer. Suitable skin penetration enhancers include but are not limited to acetone, acyl lactylates, acyl peptides, acylsarcosinates, alkanolamine salts of fatty acids, alkyl benzene sulphonates, alkyl ether sulphates, alkyl sulphates, anionic surface-active agents, benzyl benzoate, benzyl salicylate, butan-1,4-diol, butyl benzoate, butyl laurate, butyl myristate, butyl stearate, cationic surface-active agents, citric acid, cocoamidopropylbetaine, decyl methyl sulfoxide, decyl oleate, dibutyl azelate, dibutyl phthalate, dibenzyl sebacate, dibutyl sebacate, dibutyl suberate, dibutyl succinate, dicapryl adipate, didecyl phthalate, diethylene glycol, diethyl sebacate, diethyl-m-toluamide, di(2-hydroxypropyl) ether, diisopropyl adipate, diisopropyl sebacate, N,N-dimethyl acetamide, dimethyl azelate, N,N- dimethyl formamide, 1,5-dimethyl-2-pyrrolidone, dimethyl sebacate, dimethyl sulphoxide, dioctyl adipate, dioctyl azelate, dioctyl sebacate, 1,4 dioxane, 1-dodecylazacyloheptan-2-one, dodecyl dimethyl amine oxides, ethyl caprate, ethyl caproate, ethyl caprylate, 2-ethyl-hexyl pelargonate, ethyl-2-hydroxypropanoate, ethyl laurate, ethyl myristate, 1-ethyl-2-pyrrolidone, ethyl salicylate, hexyl laurate, 2-hydroxyoctanoic acid, 2-hydroxypropanoic acid, 2-hydroxypropionic acid, isethionates, isopropyl isostearate, isopropyl palmitate, guar hydroxypropyltrimonium chloride, hexan-2,5-diol, khellin, lamepons, lauryl alcohol, maypons, metal salts of fatty acids, methyl nicotinate, 2-methyl propan-2-ol, 1-methyl-2-pyrrolidone, 5-methyl-2-pyrrolidone, methyl taurides, miranol, nonionic surface-active agents, octyl alcohol, octylphenoxy polyethoxyethanol, oleic ethanolamide, pleyl alcohol, pentan-2,4-diol, phenoxyethanol, phosphatidyl choline, phosphine oxides, polyalkoxylated ether glycollates, poly(diallylpiperidinium chloride), poly(dipropyldiallylammonium chloride), polyglycerol esters, polyoxyethylene lauryl ether, polyoxy:polyoxyethylene stearate, polyoxypropylene 15 stearyl ether, poly(vinyl pyridinium chloride), propan-1-ol, propan-2-ol, propylene glycol dipelargonate, pyroglutamic acids, 2-pyrrolidone, pyruvic acids, Quaternium 5, Quaternium 18, Quaternium 19, Quaternium 23, Quaternium 31, Quaternium 40, Quaternium 57, quartenary amine salts, quaternised poly (dimethylaminoethylmethacrylate), quaternised poly (vinyl alcohol), sapamin hydrochloride, sodium cocaminopropionate, sodium dioctyl sulphonsuccinate, sodium laurate, sodium lauryl ether sulphate, sodium lauryl sulphate, sugar esters, sulphosuccinate, tetrahydrofuran, tetrahydrofurfural alcohol, transcutol, triethanolamine dodecyl benzene sulphonate, triethanolarnine oleate, urea, water and derivatives, esters, salts and mixtures thereof.

Propellants

Examples of suitable propellants include volatile hydrocarbons such as butane, propane, isobutane and fluorocarbon gases, or mixtures thereof.

In certain embodiments, fluorohydrocarbon propellants, other than chloro-fluoro carbons (CMCs) which are non-ozone-depleting propellants, are particularly useful in the production of a non-flammable foamable composition.

Such propellants include, but are not limited to hydrofluorocarbon (HFC) propellants, that contain no chlorine atoms, and as such, falls completely outside concerns about stratospheric ozone destruction by chlorofluorocarbons or other chlorinated hydrocarbons. Exemplary non-flammable propellants according to this aspect of the invention include propellants made by DuPont under the registered trademark Dymel, such as 1,1,1,2 tetrafluorethane (Dymel 134), and 1,1,1,2,3,3,3 heptafluoropropane (Dymel 227), 1,1, difluoro ethane (Dymel 152) and 1,1,1,3,3,3 hexafluoropropane. HFCs possess Ozone Depletion Potential of 0.00 and thus, they are allowed for use as propellant in aerosol products.

The propellant makes up about 5-25 wt % of the foamable composition. Aerosol propellants are used to generate and administer the foamable composition as a foam. The total composition including propellant, foamable compositions and optional ingredients is referred to as the foamable composition.

Hygroscopic Property of the Composition

A hygroscopic substance is a substance that absorbs water readily from its surroundings. Microorganisms require water to grow and reproduce, and such water requirements are best defined in terms of water activity of the substrate. The water activity of a solution is expressed as Aw=P/Po, where P is the water vapor pressure of the solution and Po is the vapor pressure of pure water at the same temperature. Addition of a hygroscopic substance to an aqueous solution in which a microorganism is growing will have the effect of lowering the Aw, with a consequent effect upon cell growth. Every microorganism has a limiting Aw, below which it will not grow, e.g., for *streptococci, klebsiella* spp., *escherichia coli, clostridium perfringens*, and *pseudomonas* spp. the Aw value is 0.95. *Staphylococcus aureus* is most resistant and can proliferate with an Aw as low as 0.86.

The water activity of a product can be determined from the relative humidity of the air surrounding the sample when the air and the sample are at equilibrium. Measurement is performed by placing a sample in an enclosed space where this equilibrium can take place. Once this occurs, the water activity of the sample and the relative humidity of the air are equal. The measurement taken at equilibrium is called an equilibrium relative humidity or ERH. The relationship between the water activity and ERH is in accordance with the following formula:

$$Aw=ERH/100$$

Various types of water activity instruments are commercially available. One exemplary instrument uses chilled-mirror dewpoint technology while other instruments measure relative humidity with sensors that change electrical resistance or capacitance.

Polyols, PEGs and other polar solvents have a great affinity for water, and as such, they exhibit hygroscopic properties. The concentration of the polyol, the PEG and/or other polar solvents determines the Aw of the carrier. In one or more embodiments, the polyols, the PEG and/or the secondary polar solvent is contained in the composition of the present invention at a sufficient concentration to provide an Aw value of the hygroscopic carrier of less than 0.9. In other embodiments, the concentration of the polyol, the PEG and/or secondary polar solvent in the composition is selected to provide a Aw value selected from the ranges of (1) about 0.8 and about 0.9; (2) about 0.7 and about 0.8; and (3) less than about 0.7.

As such, a composition containing a polyol, a PEG with or without a secondary polar solvent can be used as topical treatment of superficial infectious conditions.

The advantage of providing a hygroscopic composition in a pressurized packaging presentation is readily perceived. The usage of all other presentations, such as solutions, creams, lotions, ointments and the like involves repeated opening of the package closure, resulting in absorption of water from the surrounding environment and a subsequent elevation of the Aw (thus lowering the hygroscopicity of the product, and therefore decreasing its anti-infective potential. By contrast, a pressurized packaging does not allow for any humidity to be absorbed by the preparation, and therefore, the hygroscopic character of the composition cannot be damaged.

In one or more embodiments, the hygroscopic composition of the present invention further contains an anti-infective agent, selected from the group of an antibiotic agent, an antibacterial agent, an antifungal agent, an agent that controls yeast, an antiviral agent and an antiparasitic agent. Combining the anti-infective effect of a hygroscopic composition, which acts through a dehydration mechanism, with an additional anti-infective agent that acts through alternate mechanisms results in a synergistic effect and consequently higher success rate of the treatment.

Composition and Foam Physical Characteristics and Advantages

A pharmaceutical or cosmetic composition manufactured using the foamable carrier of the present invention is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foamable composition of the present invention is stable, having an acceptable shelf-life of at least one year, or preferably, at least two years at ambient temperature, as revealed in accelerated stability tests. Organic carriers and propellants tend to impair the stability of emulsions and to interfere with the formation of stable foam upon release from a pressurized container. It has been observed, however, that the foamable compositions according to the present invention are surprisingly stable. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam.

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administrable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

As further aspect of the foam is breakability. The breakable foam is thermally stable, yet breaks under sheer force. Sheer-force breakability of the foam is clearly advantageous over thermally induced breakability. Thermally sensitive foams immediately collapse upon exposure to skin temperature and, therefore, cannot be applied on the hand and afterwards delivered to the afflicted area.

The foam of the present invention has several advantages, when compared with hydroalcoholic foam compositions, such as described in WO 2004/071479:

(1) Breakability. The foam of the present invention is thermally stable. Unlike hydroalcoholic foam compositions of the prior art, the foam of the present invention is not "quick breaking", i.e., it does not readily collapse upon exposure to body temperature environment. Sheer-force breakability of the foam is clearly advantageous over thermally induced breakability, since it allows comfortable application and well directed administration to the target area.

(2) Skin drying and skin barrier function. Short chain alcohols are known to dry the skin and impair the integrity of the skin barrier. By contrast, including a film forming agent in the composition of the present invention foes not cause unwanted skin barrier damage.

(3) Irritability. Due to the lack of alcohol and improvement in skin barrier function, skin irritability is eliminated.

Another property of the foam is specific gravity, as measured upon release from the aerosol can. Typically, foams have specific gravity of less than 0.12 g/mL; or less than 0.10 g/mL; or less than 0.08 g/mL, depending on their composition and on the propellant concentration.

Pharmaceutical Composition

The foamable composition of the present invention is an ideal vehicle for active pharmaceutical ingredients and active cosmetic ingredients. In the context of the present invention, active pharmaceutical ingredients and active cosmetic ingredients are collectively termed "active agent" or "active agents". A foamable composition, comprising an active agent has the following advantages:

1. The foamable composition provides a preferred solvent for active agents, particularly water-insoluble agents.

2. The inclusion of a polyol and/or a PEG and a secondary polar solvent in the foamable composition facilitates a co-solvent effect, resulting increased concentrations of soluble active agent in the dosage form, thus facilitating enhanced skin penetration of the active agent. In many cases, increased penetration is positively-correlated with improved clinical outcome. In certain case, attaining an increased drug penetration into the target site of action enables a decrease of treatment frequency, for example, from twice or three times daily to once daily.

3. Polyols and PEGs; and combinations of a polyol and/or PEG with a secondary polar solvent are known as skin penetration enhancers, thus, increasing drug residence in the target area and increasing clinical efficacy, as detailed above.

4. The fact that the composition contains no water, or up to 25% and more preferably up to 10% water minimizes the probability of degradation of water-sensitive active agents. Furthermore, as exemplified herein, a foam containing a polyol and/or PEG with no water at all can be formed in accordance with the composition and process of the present invention. Such compositions ensure high stability of water sensitive active agents.

5. Combining the anti-infective effect of a hygroscopic composition, which acts through a dehydration mechanism, with an additional anti-infective agent, selected from the group of an antibiotic agent, an antibacterial agent, an antifungal agent, an agent that controls yeast, an antiviral agent-and an antiparasitic agent, that acts through alternate mechanisms results in a synergistic effect and consequently higher success rate of the treatment.

6. The foamable polyol composition in contained in an impermeable pressurized packaging presentation is impermeable and thus, the active agent is not exposed to environmental degradation factors, such as light and oxidating agent during storage.

Thus, in a preferred embodiment of the present invention, the composition includes at least one active agent.
  a. a therapeutically effective concentration of an active agent; and
  b. about 50% to about 98% of a polar solvent, selected from the group consisting of a polyol and a polyethylene glycol;
  c. 0% to about 48% of a secondary polar solvent;
  d. about 0.2% to about 5% by weight of a surface-active agent;
  e. about 0.01% to about 5% by weight of at least one polymeric agent; and
  f. a liquefied or compressed gas propellant at a concentration of about 3% to about 25% by weight of the total composition.

In the context of combining a hygroscopic carrier according to the present invention and an anti-infective active agent, a pharmaceutical composition is provided, including:
  a. a hygroscopic substance at a sufficient concentration to provide an Aw value of the hygroscopic carrier of less than 0.9. The concentration of the hygroscopic substance in the composition can be designed to provide a Aw value selected from the ranges of (1) about 0.8 and about 0.9; (2) about 0.7 and about 0.8; and (3) less than about 0.7.;
  b. about 0.2% to about 5% by weight of a surface-active agent;
  c. about 0.01% to about 5% by weight of at least one polymeric agent selected from a bioadhesive agent, a gelling agent, a film forming agent and a phase change agent;
  d. a therapeutically effective concentration of an anti-infective agent; and
  e. a liquefied or compressed gas propellant at a concentration of about 3% to about 25% by weight of the total composition.

An exemplary case for the inclusion of an anti-infective agent in a hygroscopic composition is provided herewith. It has been surprisingly discovered that combining an antifungal agent in a hygroscopic composition results in an anti-infective effect on strains that are not supposed to be affected by the said antifungal agent. For example, terbinafine is know to be highly effective against dermatophite pathogens, but not against *candida*. In-vitro studies have revealed, however that terbinafine, dissolved in a hygroscopic carrier, effectively inhibited the spreading of *candida albicans*, while a control preparation, comprising the same concentration of terbinafine in an emulsion base was not effective. Thus, combining an antifungal agent in a hygroscopic composition results in an expansion of the spectrum of infective strains that can benefit form the therapy, and furthermore, in can render an improved effect of such a composition on mixed infections or in infections that are not accurately diagnosed.

Consequently, in another aspect of the present invention, a pharmaceutical composition, which possesses an improved antifungal activity or that possesses an antifungal activity on an expanded spectrum of pathogens, is provided, including:
  a. a hygroscopic composition, comprising a hygroscopic substance at a sufficient concentration to provide an Aw value of the hygroscopic carrier of less than 0.9. The concentration of the hygroscopic substance in the composition can be designed to provide a Aw value selected from the ranges of (1) about 0.8 and about 0.9; (2) about 0.7 and about 0.8; and (3) less than about 0.7.;
  b. an anti-infective agent, selected from the group of an antibiotic agent, an antibacterial agent, an antifungal agent, an agent that controls yeast, an antiviral agent and an antiparasitic agent. Preferably, the anti-infective agent is an antifungal agent, and more preferably the anti-infective agent is terbinafine.

Active Agents

Suitable active agents include but are not limited to active herbal extracts, acaricides, age spot and keratose removing agents, allergen, analgesics, local anesthetics, antiacne agents, antiallergic agents, antiaging agents, antibacterials, antibiotics, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antipsoriatic agents, antirosacea agents antiseborrheic agents, antiseptic, antiswelling agents, antiviral agents, antiyeast agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, non-steroidal anti-inflammatory agents, oxidizing agents, pediculicides, photodynamic therapy agents, retinoids, sanatives, scabicides, self tanning agents, skin whitening agents, asocontrictors, vasodilators, vitamins, vitamin D derivatives, wound healing agents and wart removers. As is known to one skilled in the art, in some instances a specific active active agent may have more than one activity, function or effect.

In an embodiment of the present invention, the active agent is an active herbal extract. Suitable active herbal extracts include but are not limited to angelica, anise oil, astragali radix, azalea, benzyl acetate, birch tar oil, bomyl acetate, cacumen biotae, camphor, cantharidin, *capsicum*, cineole, cinnamon bark, cinnamon leaf, citronella, citroneliol, citronellyl acetate, citronellyl formate, eucalyptus, eugenyl acetate, flos carthami, fructus mori, garlic, geraniol, geranium, geranyl acetate, habanera, isobutyl angelicate, lavender, ledum latifolium, ledum palustre, lemongrass, limonene, linalool, linalyl acetate, methyl anthranilate, methyl cinnamate, mezereum, neem, nerol, neryl acetate, nettle root extract, oleum ricini, oregano, pinenes, alpha.-pinene, .beta.-pinene, radix angelicae sinesis, radix paenoiae rubra, radix polygoni multiflori, radix rehmanniae, *rhizoma pinelliae, rhizoma zingiberis recens*, sabadilla, sage, sandalwood oil, saw palmetto extract, semen sesami nigrum, staphysagria, tea tree oil, terpene alcohols, terpene hydrocarbons, terpene esters, terpinene, terpineol, terpinyl acetate and derivatives, esters, salts and mixtures thereof. In an embodiment of the present invention, the active agent is an acaricide. Suitable acaricides include but are not limited to amitraz, flumethrin, fluvalinate and derivatives, esters, salts and mixtures thereof.

In an embodiment of the present invention, the active agent is an age spot and keratoses removing agent. Suitable age spot and keratoses removing agent include but are not limited to hydroxy acids, azelaic acid and other related dicarboxylic acids, retinoids, kojic acid, arbutin, nicotinic, ascorbic acid, hydroquinone and derivatives, esters, salts and mixtures thereof. Certain nonsteroidal anti-inflammatory agents, such as diclofenac are also useful for the treatment of keratoses.

In an embodiment of the present invention, the active agent is an analgesic. Suitable analgesics include but are not limited to benzocaine, butamben picrate, dibucaine, dimethisoquin, dyclonine, lidocaine, pramoxine, tetracaine, salicylates and derivatives, esters, salts and mixtures thereof.

In an embodiment of the present invention, the active agent is a local anesthetic. Suitable local anesthetics include but are not limited to benzocaine, benzyl alcohol, bupivacaine, butamben picrate, chlorprocaine, cocaine, dibucaine, dimethisoquin, dyclonine, etidocaine, hexylcaine, ketamine, lidocaine, mepivacaine, phenol, pramoxine, procaine, tetracaine, salicylates and derivatives, esters, salts and mixtures thereof.

In an embodiment of the present invention, the active agent is an antiacne agent. Suitable antiacne agents include but are not limited to N-acetylcysteine, adapalene, azelaic acid, benzoyl peroxide, cholate, clindamycin, deoxycholate, erythromycin, flavinoids, glycolic acid, meclocycline, metronidazol, mupirocin, octopirox, phenoxy ethanol, phenoxy proponol, pyruvic acid, resorcinol, retinoic acid, salicylic acid, scymnol sulfate, sulfacetamide-sulfur, sulfur, tazarotene, tetracycline, tretinoin triclosan and derivatives, esters, salts and mixtures thereof.

In an embodiment of the present invention, the active agent is an antiaging agent. Suitable antiaging agents include but are not limited to sulfur-containing D and L amino acids, alpha-hydroxy acids s, beta-hydroxy acids (e.g. salicylic acid), urea, hyaluronic acid, phytic acid, lipoic acid; lysophosphatidic acid, skin peel agents (e.g., phenol, resorcinol and the like), vitamin B3 compounds (e.g., niacinamide, nicotinic acid and nicotinic acid salts and esters, including nonvasodilating esters of nicotinic acid (such as tocopheryl nicotinate), nicotinyl amino acids, nicotinyl alcohol esters of carboxylic acids, nicotinic acid N-oxide and niacinamide N-oxide), vitamin B5 and retinoids (e.g., retinol, retinal, retinoic acid, retinyl acetate, retinyl palmitate, retinyl ascorbate) skin barrier forming agents, melatonin and derivatives, esters, salts and mixtures thereof.

In an embodiment of the present invention, the active agent is an antibiotic. The terms "antibiotic" as used herein shall include, but is not limited to, any substance being destructive to or inhibiting the growth of bacteria or any substance having the capacity to inhibit the growth of or to destroy bacteria. In one or more embodiments, the antibiotic agent is selected from the group consisting of a beta-lactam antibiotic, an aminoglycoside, an ansa-type antibiotic, an anthraquinone, an azole, an antibiotic glycopeptide, a macrolide, an antibiotic nucleoside, an antibiotic peptide, an antibiotic polyene, an antibiotic polyether, an antibiotic quinolone, an antibiotic steroid, a sulfonamide, an antibiotic metal, an oxidizing agent, a periodate, a hypochlorite, a permanganate, a substance that release free radicals and/or active oxygen, a cationic antimicrobial agent, a quaternary ammonium compound, a biguanide, a triguanide, a bisbiguanide, a polymeric biguanide, and analogs, derivatives, salts, ions and complexes thereof.

Suitable antibiotics include but are not limited to amanfadine hydrochloride, amanfadine sulfate, amikacin, arnikacin sulfate, aminoglycosides, amoxicillin, ampicillin, ansamycins, bacitracin, beta-lactams, candicidin, capreomycin, carbenicillin, cephalexin, cephaloridine, cephalothin, cefazolin, cephapirin, cephradine, cephaloglycin, chloramphenicols, chlorhexidine, chlorhexidine gluconate, chlorhexidine hydrochloride, chloroxine, chlorquinaldol, chlortetracycline, chlortetracycline hydrochloride, ciprofloxacin, circulin, clindamycin, clindamycin hydrochloride, clotrimazole, cloxacillin, demeclocycline, diclosxacillin, diiodohydroxyquin, doxycycline, ethambutol, ethambutol hydrochloride, erythromycin, erythromycin estolate, erythromycin stearate, farnesol, floxacillin, gentamicin, gentamicin sulfate, gramicidin, griseofulvin, haloprogin, haloquinol, hexachlorophene, iminocyldline, iodate, iodine, iodochlorhydroxyquin, kanamycin, kanamycin sulfate, lincomycin, lineomycin, lineomycin hydrochloride, macrolides, meclocycline, methacycline, methacycline hydrochloride, methenamine, methenamine hippurate, methenamine mandelate, methicillin, metronidazole, miconazole, miconazole hydrochloride, microcrystalline and nanocrystalline particles of silver, copper, zinc, mercury, tin, lead, bismuth, cadmium and chromium, minocycline, minocycline hydrochloride, mupirocin, nafcillin, neomycin, neomycin sulfate, netilmicin, netilmicin sulfate, nitrofurazone, norfloxacin, nystatin, octopirox, oleandomycin, orcephalosporins, oxacillin, oxytetracycline, oxytetracycline hydrochloride, parachlorometa xylenol, paromomycin, paromomycin sulfate, penicillins, penicillin G, penicillin V, pentamidine, pentamidine hydrochloride, phenethicillin, polymyxins, quinolones, streptomycin sulfate, tetracycline, tobramycin, tolnaftate, triclosan, trifampin, rifamycin, rolitetracycline, spectinomycin, spiramycin, streptomycin, sulfonamide, tetracyclines, tetracycline, tobramycin, tobramycin sulfate, triclocarbon, triclosan, trimethoprim-sulfamethoxazole, tylosin, vancomycin, yrothricin and derivatives, esters, salts and mixtures thereof.

In an embodiment of the present invention, the active agent is an antidandruff agent. Suitable antidandruff agents include but are not limited to aminexil, benzalkonium chloride, benzethonium chloride, 3-bromo-1-chloro-5,5-dimethyl-hydantoin, chloramine B, chloramine T, chlorhexidine, N-chlorosuccinimide, climbazole-1,3-dibromo-5,5-dimethylhydantoin, 1,3-dichloro-5,5-dimethyl-hydantoin, betulinic acid, betulonic acid, celastrol, crataegolic acid, cromakalin, cyproterone acetate, dutasteride, finesteride, ibuprofen, ketoconozole, oleanolic acid, phenytoin, picrotone olamine, salicylic acid, selenium sulphides, triclosan, triiodothyronine, ursolic acid, zinc gluconate, zinc omadine, zinc pyrithione and derivatives, esters, salts and mixtures thereof.

In an embodiment of the present invention, the active agent is an antihistamine. Suitable antihistamines include but are not limited to chlorcyclizine, diphenhydramine, mepyramine, methapyrilene, tripelennamine and derivatives, esters, salts and mixtures thereof.

In an embodiment of the present invention, the active agent is an antimycotic Also termed antifungal agent. The terms "antimycotic" and "antifungal" as used herein include, but is not limited to, any substance being destructive to or inhibiting the growth of fungi and yeast or any substance having the capacity to inhibit the growth of or to destroy fungi and/or yeast.

In one or more embodiments, the antifungal agent is an agent that is useful in the treatment of a superficial fungal infection of the skin, dermatophytosis, microsporum, trichophyton and epidermophyton infections, candidiasis, oral candidiasis (thrush), candidiasis of the skin and genital mucous membrane, *candida paronychia*, which inflicts the nail and nail bed and genital and vaginal *candida*, which inflict genitalia and the vagina.

Suitable antimycotics include but are not limited to allylamines, amorolfine, amphotericin B, azole compounds, bifonazole, butoconazole, chloroxine, clotrimazole, ciclopirox olamine, clotrimazole, econazole, elubiol, fenticonazole, fluconazole, flucytosine (5FC), griseofulvin, itraconazole, ketoconazole, mafenide acetate, miconazole, naftifine, natamycin, tolnaftate, nystatin, polyenes, oxiconazole, sulbentine, sulconazole, terbinafine, terconazole, tioconazole, undecylenic acid and derivatives, esters, salts and mixtures thereof.

In an embodiment of the present invention, the active agent is an antipruritic. Suitable antipruritics include but are not limited to menthol, methdilazine, trimeprazine, urea and derivatives, esters, salts and mixtures thereof.

In an embodiment of the present invention, the active agent is an additional antipsoriatic agent. Suitable additional antipsoriatic agents include but are not limited to 6-aminonicotinamide, 6-aminonicotinic acid, 2-aminopyrazinamide, anthralin, 6-carbamoylnicotinamide, 6-chloronicotinamide, 2-carbamoylpyrazinamide, corticosteroids, 6-dimethylaminonicotinamide, dithranol, 6-formylaminonicotinamide, 6-hydroxy nicotinic acid, 6-substituted nicotinamides, 6-substituted nicotinic acid, 2-substituted pyrazinamide, tazarotene, thionicotinamide, trichothecene mycotoxins and derivatives, esters, salts and mixtures thereof.

In an embodiment of the present invention, the active agent is an antirosacea agent. Suitable antirosacea agents include but are not limited to azelaic acid, metronidazole, sulfacetamide and derivatives, esters, salts and mixtures thereof. Certain nonsteroidal anti-inflammatory agents, such as salicylic acid, salycilates, piroxicam and diclofenac are also useful for the treatment of Rosacea.

In an embodiment of the present invention, the active agent is an antiseborrheic agent. Suitable antiseborrheic agents include but are not limited to glycolic acid, salicylic acid, selenium sulfide, zinc pyrithione, a dicarboxylic acid, such as azelaic acid and derivatives, esters, salts and mixtures thereof.

In an embodiment of the present invention, the active agent is an antiviral agent. Suitable antiviral agents include but are not limited to acyclovir, gancyclovir, ribavirin, amantadine, rimantadine nucleoside-analog reverse transcriptase inhibitors, such as zidovudine, didanosine, zalcitabine, tavudine, lamivudine and vidarabine, non-nucleoside reverse transcriptase inhibitors, such as nevirapine and delavirdine, protease inhibitors, such as saquinavir, ritonavir, indinavir and nelfinavir, and interferons and derivatives, esters, salts and mixtures thereof.

In an embodiment of the present invention, the active agent is a chemotherapeutic agent. Suitable chemotherapeutic agents include but are not limited to daunorubicin, doxorubicin, idarubicin, amrubicin, pirarubicin, epirubicin, mitoantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A, XR9576 and derivatives, esters, salts and mixtures thereof.

In an embodiment of the present invention, the active agent is a corticosteroid. Suitable corticosteroids include but are not limited to alclometasone dipropionate, amcinafel, amcinafide, amcinonide, beclomethasone, beclomethasone dipropionate, betamethsone, betamethasone benzoate, betamethasone dexamethasone-phosphate, dipropionate, betamethasone valerate, budesonide, chloroprednisone, chlorprednisone acetate, clescinolone, clobetasol, clobetasol propionate, clobetasol valerate, clobetasone, clobetasone butyrate, clocortelone, cortisone, cortodoxone, craposone butyrate, desonide, desoxymethasone, dexamethasone, desoxycorticosterone acetate, dichlorisone, diflorasone diacetate, diflucortolone valerate, diflurosone diacetate, diflurprednate, fluadrenolone, flucetonide, flucloronide, fluclorolone acetonide, flucortine butylesters, fludroxycortide, fludrocortisone, flumethasone, flumethasone pivalate, flumethasone pivalate, flunisolide, fluocinolone, fluocinolone acetonide, fluocinonide, fluocortin butyl, fluocortolone, fluorometholone, fluosinolone acetonide, fluperolone, fluprednidene acetate, fluprednisolone hydrocortamate, fluradrenolone, fluradrenolone acetonide, flurandrenolone, fluticasone, halcinonide, halobetasol, hydrocortisone, hydrocortisone acetate, hydrocortisone butyrate, hydrocortisone cyclopentylpropionate, hydrocortisone valerate, hydroxyltriamcinolone, medrysone, meprednisone, .alpha.-methyl dexamethasone, methylprednisolone, methylprednisolone acetate, mometasone furoate, paramethasone, prednisolone, prednisone, pregnenolone, progesterone, spironolactone, triamcinolone, triamcinolone acetonide and derivatives, esters, salts and mixtures thereof.

In an embodiment of the present invention, the active agent is a hair growth regulator. Suitable hair growth regulators include but are not limited to N-acetylgalactosamine, N-acetylglucosamine, N-acetylmannosamine, acitretin, aminexil, ascomycin, asiatic acid, azelaic acid, benzalkonium chloride, benzethonium chloride, benzydamine, benzyl nicotinate, benzoyl peroxide, benzyl peroxide, betulinic acid, betulonic acid, calcium pantothenate, celastrol, cepharanthine, chlorpheniramine maleate, clinacycin hydrochloride, crataegolic acid, cromakalin, cyproterone acetate, diazoxide, diphenhydramine hydrochloride, dutasteride, estradiol, ethyl-2-hydroxypropanoate, finasteride, D-fucono-1,5-lactone, furoate, L-galactono-1,4-lactone, D-galactosamine, D-glucaro-1,4-lactone, D-glucosamine-3-sulphate, hinokitiol, hydrocortisone, 2-hydroxypropionic acid, isotretinoin, itraconazole, ketoconazole, latanoprost, 2-methyl propan-2-ol, minocyclin, minoxidil, mipirocin, mometasone, oleanolic acid, panthenol, 1,10-phenanthroline, phenytoin, prednisolone, progesterone, propan-2-ol, pseudoterins, resorcinol, selenium sulfide, tazarotene, triclocarbon, triclosan, triiodothyronine, ursolic acid, zinc pyrithione and derivatives, esters, salts and mixtures thereof.

In an embodiment of the present invention, the active agent is a hormone. Suitable hormones include but are not limited to methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5a-dihydrostosterone, testolactone, 17a-methyl-19-nortestosterone, desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogrestrel, trimegestone, gestodene, nomegestrol acetate, progesterone, 5a-pregnan-3b,20a-diol sulfate, 5a-pregnan-3b,20b-diol sulfate, 5a-pregnan-3b-ol-20-one, 16,5a-pregnen-3b-ol-20-one, 4-pregnen-20b-ol-3-one-20-sulfate, acetoxypregnenolone, anagestone acetate, cyproterone, dihydrogesterone, flurogestone acetate, gestadene, hydroxyprogesterone acetate, hydroxymethylprogesterone, hydroxymethyl progesterone acetate, 3-ketodesogestrel, megestrol, melengestrol acetate, norethisterone, progestins and derivatives, esters, salts and mixtures thereof.

In an embodiment of the present invention, the active agent is a hydroxyacid. Suitable hydroxy acids include but are not limited to agaricic acid, aleuritic acid, allaric acid, altraric acid, arabiraric acid, ascorbic acid, atrolactic acid, benzilic acid, citramalic acid, citric acid, dihydroxytartaric acid, erythraric acid, galactaric acid, galacturonic acid, glucaric acid, glucuronic acid, glyceric acid, glycolic acid, gularic acid, gulonic acid, hydroxypyruvic acid, idaric acid, isocitric acid, lactic acid, lyxaric acid, malic acid, mandelic acid, mannaric acid, methyllactic acid, mucic acid, phenyllactic acid, pyruvic acid, quinic acid, ribaric acid, ribonic acid, saccharic acid, talaric acid, tartaric acid, tartronic acid, threaric acid, tropic acid, uronic acids, xylaric acid and derivatives, esters, salts and mixtures thereof.

In an embodiment of the present invention, the active agent is a keratolytic agent. The term "keratolytic agent" is used herein to mean a compound which loosens and removes the stratum corneum of the skin, or alters the structure of the keratin layers of skin. Keratolytic agents are used in the treatment of many dermatological disorders, which involve dry skin, hyperkeratiinization (such as prsoriasis), skin itching (such as xerosis), acne and rosacea. Suitable keratolytic agents include but are not limited to N-acetylcysteine, azelaic acid, cresols, dihydroxy benzene compounds, such as resorcinol and hydroquinone, alpha-hydroxy acids, such as lactic acid and glycolic acid, phenol, pyruvic acid, resorcinol, sulfur, salicylic acid, retinoic acid, isoretinoic acid, retinol, retinal, urea and derivatives, esters, salts and mixtures thereof.

In an embodiment of the present invention, the active agent is a lactam. Suitable lactams include but are not limited to L-galactono-1,4-lactam, L-arabino-1,5-lactam, D-fucono-1,5-lactam, D-glucaro-1,4-lactam, D-glucurono-6,3-lactam, 2,5-tri-O-acetyl-D-glucurono-6,3-lactam, 2-acetamido-2-deoxyglucono-1,5-l-actam, 2-acetamido-2-deoxygalactono-1,5-lactam, D-glucaro-1,4:6,3-dilactam-, L-idaro-1,5-lactam, 2,3,5,tri-O-acetyl-D-glucaro-1,4-lactam, 2,5-di-O-acetyl-D-glucaro-1,4:6,3-dilactam, D-glucaro-1,5-lactam methyl ester, 2-propionoamide-2-deoxyglucaro-1,5-lactam and derivatives, esters, salts and mixtures thereof.

In an embodiment of the present invention, the active agent is a non-steroidal anti-inflammatory agent. Suitable non-steroidal anti-inflammatory agent include but are not limited to azelaic acid, oxicams, piroxicam, isoxicam, tenoxicam, sudoxicam, CP-14,304, salicylates, aspirin, disalcid, benorylate, trilisate, safapryn, solprin, diflunisal, fendosal, acetic acid derivatives, diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac, fenamates, mefenamic, meclofenamic, flufenamic, niflumic, tolfenamic acids, propionic acid derivatives, ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofen, pyrazoles, phenylbutazone, oxyphenbutazone, feprazone, azapropazone, trimethazone and derivatives, esters, salts and mixtures thereof.

In an embodiment of the present invention, the active agent is insecticide. The term "insecticide, is used herein to mean a compound which kills, inhibits the growth of, impeded the proliferation of or repels insects. Insecticides include, for example, agents that can kill lice, flees, ticks, mites, scabies and mousquitos, as well as agents that repel such insects. Suitable insecticides include but are not limited to DDT, lindane, malathion, permethrin, allethrin, biopermethrin, transpermethrin, phenothrin, diethyl-m-toluamide, dimethyl phthalate, piperonyl butoxide, pyrethroids and derivatives, esters, salts and mixtures thereof.

In an embodiment of the present invention, the active agent is a vasodilator. Suitable vasodilators include but are not limited to agents that modulate the activity of the enzyme nitric oxide synthase, nicotinic acid, ethyl nicotinate, amyl nitrite, amyl nitrate, ethyl nitrite, butyl nitrite, isobutyl nitrite, glyceryl trinitrate, octyl nitrite, sodium nitrite, sodium nitroprusside, clonitrate, erythrityl tetranitrate, isosorbide mononitrate, isosorbide dinitrate, mannitol hexanitrate, pentaerythritol tetranitrate, penetrinitol, triethanolamine trinitrate, trolnitrate phosphate (triethanolamine trinitrate diphosphate), propatylnitrate, nitrite esters of sugars, nitrite esters of polyols, nitrate esters of sugars, nitrate esters of polyols, nicorandil, apresoline, diazoxide, hydralazine, hydrochlorothiazide, minoxidil, pentaerythritol, tolazoline, scoparone, a beta-adrenergic blocker, an alpha-adrenoceptor blocker, a prostaglandin, sildenafil, dipyridamole, catecholamine, isoproternol, furosemide, prostaglandin, prostacyclin, enalaprilat, morphine, acepromazine, prazosin (α-blocker), enalapril, Captopril, amlodipine, minoxidil, tadalafil, vardenafil, phenylephrin, etilefein, caffeine, capsaicin, an extract *capsicum*, *achillea millefolium* (Yarrow), *allium sativum* (garlic), *amoracia rusticana* (horseradish), *berberis vulgaris* (barberry), *cimicifuga racemosa* (black cohosh), *coleus forskholii* (coleus), *coptis* (goldenthread), *crataegus* (hawthorn), *eleutherococcus senticosus* (siberian ginseng), *ginkgo biloba* (ginkgo), *melissa offiicnalis* (lemon balm), *olea europaea* (olive leaf), *panax ginseng* (Chinese ginseng), *petroselinum crispum* (parsley), *scutellaria baicalensis* (baical skullcap), *tilia Europaea* (linden flower), *trigonella foenum-graecum* (fenugreek), *urtica dioica* (nettles), *valeriana officinalis* (valerian), *viburnum* (cramp, bark, black haw), *veratrum viride* (American hellebore), *verbena officinalis* (vervain), *xanthoxylum americanum* (prickly ash), *zingiber officinale* (ginger), *rauwolfia serpentina* (Indian snakeroot), *viscum album*, wild yam, sasparilla, licorice, damiana, yucca, saw palmetto, gotu kola (*centella asiatica*), yohimbine and salts, hazel nut, brazil nut and walnut, and derivatives, esters, salts and mixtures thereof.

In an embodiment of the present invention, the active agent is a vasoconstrictor. Suitable vasodilators include but are not limited to ephedrine, epinephrine, phenylephrine, angiotensin, vasopressin; an extract *ephedra sinica* (ma huang), *polygonum bistorta* (bistort root), *hamamelis virginiana* (witch hazel), *hydrastis canadensis* (goldenseal), *lycopus virginicus* (bugleweed), *aspidosperma quebracho* (quebracho blanco), *cytisus scoparius* (scotch broom) and cypressand and derivatives, esters, salts and mixtures thereof.

In an embodiment of the present invention, the active agent is a retinoid. Suitable retinoids include but are not limited to retinol, retinal, retinoic acid, all-trans retinoic acid, isotretinoin, tazarotene, adapalene, 13-cis-retinoic acid, acitretin all-trans beta carotene, alpha carotene, lycopene, 9-cis-beta-carotene, lutein and zeaxanthin.

In an embodiment of the present invention, the active agent is a vitamin D analog. Suitable retinoids include but are not limited to calcipotriene, cholecalciferol, 25-hydroxycholecalciferol, 1α,25-dihydroxycholecalciferol, ergocalciferol, 1α,25-dihydroxyergocalciferol, 22,23-dihydroergocalciferol, 1,24,25-trihydroxycholecalciferol, previtamin $D_3$, tachysterol$_3$ (also termed tacalciol), isovitamin $D_3$, dihydrotachysterol$_3$, (1S)-hydroxycalciol, (24R)-hydroxycalcidiol, 25-fluorocalciol, ercalcidiol, ertacalciol, (5E)-isocalciol, 22,23-dihydroercalciol, (24S)-methylcalciol, (5E)-(10S)-10,19-dihydroercalciol, (24S)-ethylcalciol and (22E)-(24R)-ethyl-22,23-didehydrocalciol. In a preferred embodiment, the vitamin D analog is calcipotriene, which is useful in the treatment of psoriasis.

In an embodiment of the present invention, the active agent is selected from the group consisting of an immunosuppressants and immunoregulating agents. Suitable immunosuppressants and immunoregulating agents include but are not limited to cyclic peptides, such as cyclosporine, tacrolimus, tresperimus, pimecrolimus, sirolimus (rapamycin), verolimus, laflunimus, laquinimod, imiquimod derivatives, esters, salts and mixtures thereof. In one or more embodiments, the immunomodulator is a calcineurin Inhibitor.

In an embodiment of the present invention, the active agent is a wart remover. Suitable wart removers include but are not limited to imiquimod, podophyllotoxin and derivatives, esters, salts and mixtures thereof.

In an embodiment of the present invention, the active agent is a photodynamic therapy (PDT) agent. Suitable PDT agents include but are not limited to modified porphyrins, chlorins, bacteriochlorins, phthalocyanines, naphthalocyanines, pheophorbides, purpurins, m-THPC, mono-L-aspartyl chlorin e6, bacteriochlorins, phthalocyanines, benzoporphyrin derivatives, as well as photosensitiser precursors, such as aminolevulinic acid and derivatives, esters, salts and mixtures thereof.

In an embodiment of the present invention, the active agent is an antioxidant or a radical scavenger. Suitable antioxidants and radical scavengers agents include but are not limited to ascorbic acid, ascorbyl esters of fatty acids, magnesium ascorbyl phosphate, sodium ascorbyl phosphate, ascorbyl sorbate, tocopherol, tocopheryl sorbate, tocopheryl acetate, butylated hydroxy benzoic acid, 6-hydroxy-2,5,7,8-tetramethylchroman-2-carboxylic acid, gallic acid, propyl gallate, uric acid, sorbic acid, lipoic acid, diethylhydroxylamine, amino-guanidine, glutathione, dihydroxy fumaric acid, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and polyunsaturated oils, containing omega-3 and omega-6 fatty acids (e.g., linoleic and linolenic acid, gamma-linoleic acid, eicosapentaenoic acid and docosahexaenoic acid and derivatives, esters, salts and mixtures thereof.

In an embodiment of the present invention, the active agent is a self-tanning agent, such as dihydroxyacetone.

In an embodiment of the present invention, the active agent is an agent, capable of treating hyperhidrosis. Suitable hyperhidrosis agents include but are not limited to anticholinergic drugs, boric acid, tannic acid, resorcinol, potassium permanganate, formaldehyde, glutaraldehyde, methenamine, a Lewis acid, aluminum chloride, aluminum chlorohydrates, zirconium chlorohydrates, aluminum-zirconium-Glycine (AZG) complex, aluminum hydroxybromide, a glycopyrrolate compound, a 5-alpha-reductase inhibitor, finasteride, epristeride, flutamide, spironolactone, saw palmetto extract, cholestan-3-one, a mono- and dicarboxylic acid having 4 to 18 carbon atoms, botulinum toxin, a 5-HT2C receptor antagonist, a 5-HT2C receptor antagonist, ketanserin, ritanserin, mianserin, mesulergine, cyproheptadine, fluoxetine, mirtazapine, olanzapine and ziprasidone.

In an embodiment of the present invention, the active agent is a sunscreen agent. Suitable sunscreen agents include but are not limited to titanium dioxide, zinc oxide, zirconium oxide, iron oxide, p-aminobenzoic acid and its derivatives (ethyl, isobutyl, glyceryl esters; p-dimethylaminobenzoic acid); anthranilic acid derivatives (i.e., o-amino-benzoates, methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid, o- and p-hydroxybiphenyldisulfonates, coumarin derivatives (7-hydroxy, 7-methyl, 3-phenyl), diazoles (2-acetyl-3-bromoindazole, phenyl benzoxazole, methyl naphthoxazole, quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one), terephthalylidene dicamphor sulfonic acid and 4-isopropyl-di-benzoylmethane.

In an embodiment of the present invention, the active agent is a figure-forming agent and an agent, capable of treating cellulite. Suitable such agents include but are not limited to baldderwack extract, butcher's, broom, cayenne, dandelion, red clover, ginkgo biloba, horse chestnut, witch hazel and borage oil, caffeic acid, nicotinic acid, theophiline and pentoxyphilline and salts and derivatives thereof.

Several disorders of the skin, body cavity or mucosal surface (e.g., the mucosa or the cavity of the nose, mouth, eye, ear, vagina or rectum) involve a combination of etiological factors. For example, fungal and bacterial infections and that are inflamed and have symptoms of redness and/or itching warrant therapy that combines an anti-infective agent and an anti-inflammatory agent. Thus, in several cases, combining at least two active agents that treat different etiological factors results in a synergistic effect and consequently higher success rate of the treatment.

In certain cases, the composition contains two active agents, where each of the active agents require a different pH environment in order to remain stable. For example, corticosteroids are typically stable at acidic pH values (they have a maximum stability at a pH of about 4-6) and of vitamin D analogues are typically stable at basic pH values (they have a maximum stability at pH values above about 8). In order to circumvent the problem of instability it is preferred that the composition is substantially non-aqueous. The term "substantially non-aqueous" is intended to indicate that the composition has a water content below about 5%, preferably below about 2%, such as below about 1.5%.

Fields of Applications

The foamable carrier of the present invention is suitable for treating any infected surface. In one or more embodiments, foamable carrier is suitable for administration to the skin, a body surface, a body cavity or mucosal surface, e.g., the cavity and/or the mucosa of the nose, mouth, eye, ear, respiratory system, vagina or rectum (severally and interchangeably termed herein "target site").

By selecting a suitable active agent, or a combination of at least two active agents, the foamable composition of the present invention is useful in treating an animal or a human patient having any one of a variety of dermatological disorders, including dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, grannuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo.

Likewise, the foamable composition of the present invention is suitable for treating a disorder of a body cavity or mucosal surface, e.g., the mucosa of the nose, mouth, eye, ear, respiratory system, vagina or rectum. Non limiting examples of such conditions include chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

In an embodiment of the present invention, the composition is useful for the treatment of an infection. In one or more embodiments, the composition is suitable for the treatment of an infectiion, selected from the group of a bacterial infection, a fungal infection, a yeast infection, a viral infection and a parasitic infection.

In an embodiment of the present invention, the composition is useful for the treatment of wound, ulcer and burn. This use is particularly important since the composition of the present invention creates a thin, semi-occlusive layer, which coats the damaged tissue, while allowing exudates to be released from the tissue.

The composition of the present invention is also suitable for administering a hormone to the skin or to a mucosal membrane or to a body cavity, in order to deliver the hormone into the tissue of the target organ, in any disorder that responds to treatment with a hormone.

In light of the hygroscopic nature of the composition, it is further suitable for the treatment and prevention of post-surgical adhesions. Adhesions are scars that form abnormal connections between tissue surfaces. Post-surgical adhesion formation is a natural consequence of surgery, resulting when tissue repairs itself following incision, cauterization, suturing, or other means of trauma. When comprising appropriate protective agents, the foam is suitable for the treatment or prevention of post surgical adhesions. The use of foam is particularly advantageous because foam can expand in the body cavity and penetrate into hidden areas that cannot be reached by any other alternative means of administration.

The invention is described with reference to the following examples. This invention is not limited to these examples and experiments. Many variations will suggest themselves and are within the full intended scope of the appended claims.

EXAMPLE 1

Foamable Carriers Containing Polyols

| Ingredient | TECH PG-014 % W/W | TECH PG-015 % W/W | TECH PG-016 % W/W |
|---|---|---|---|
| Propylene glycol (PG) | 82.00 | 92.00 | 60.00 |
| Laureth-4 | 2.00 | 2.00 | 2.00 |
| Glyceryl stearate and PEG-100 stearate (Simulsol 165) | 4.00 | 4.00 | 3.00 |
| PEG 4000 | 10.00 | | |
| Glycerin anhydrous | | | 33.00 |
| Hydroxypropylcellulose (Klucel EF) | 2.00 | 2.00 | 2.00 |
| Total | 100.00 | 100.00 | 100.00 |
| Foam quality | Good | Good | Good |
| Shakability | Shakable | Shakable | Shakable |

Notes:

The compositions are substantially non-aqueous

Composition TECH PG-015 contains the minimum number of components that constitute a foamable composition, which upon release from an aerosol pressurized container affords foam of Good or Excellent quality. It contains a diol (PG), a polymeric agent (Klucel EF), and a non-ionic surface active agent (PEG-100 stearate and Laureth 4)

Composition TECH PG-014 demonstrates that the addition of 10% PEG (secondary polar solvent) maintains Good foam quality.

Composition TECH PG-016 demonstrates that a mixture of two polyols (PG and glycerin maintains Good foam quality. This composition possesses high skin hydration effect.

The liquefied or gas propellant can be added at a concentration of about 3% to about 25%.

EXAMPLE 2

Foamable Carriers Containing Polyols

| Ingredient | TECH PG-021 % W/W | TECH PG-024 % W/W | TECH PG-025 % W/W |
|---|---|---|---|
| Propylene glycol (PG) | 91.00 | 58.00 | 43.00 |
| Stearyl alcohol | 2.00 | 1.00 | 1.00 |
| Laureth-4 | 2.00 | 2.00 | 2.00 |
| Glyceryl stearate and PEG-100 stearate (Simulsol 165) | 3.00 | 3.00 | 3.00 |
| Glycerin | | 33.00 | 33.00 |
| Hydroxypropylcellulose (Klucel EF) | 2.00 | 3.00 | 3.00 |
| Dimethyl isosorbide (DMI) | | | 15.00 |
| Total | 100.00 | 100.00 | 100.00 |
| Foam quality | Excellent | Excellent | Excellent |
| Shakability | Shakable | Shakable | Shakable |

The following procedure was employed when the compositions of Example 2 were produced.

Step 1: Preparation of Phase A
1. Heat Propylene glycol and stearyl alcohol to 80-85° C.
2. Add Klucel while mixing.
3. Cool to 70-75° C. Add all other ingredients while mixing. Agitation continues until solution uniformity is reached
4. Cool solution to 30° C. whith moderate mixing.

Step 2: Canisters Filling and Crimping

1. Each aerosol canister 35×70 mm is filled with 30±5% g of the composition

2. Each canister was closed with an aerosol valve, using a vacuum crimping machine.

Step 3: Pressurizing

Propellant (mix of propane, butane and isobutane) was added to each of the canisters Notes:

Composition TECH PG-021, 24 and 25 demonstrates that the addition of 1-2% stearyl alcohol (foam adjuvant) facilitates the formation of foam with Excellent quality. Substituting Stearyl alcohol with stearic acid results in an excellent foam too.

Composition TECH PG-025 demonstrates that the addition of 15% DMI (foam adjuvant) facilitates the formation of foam with Excellent quality. This composition possesses high skin penetration enhancing properties.

The liquefied or gas propellant can be added at a concentration of about 3% to about 25%.

EXAMPLE 3

Foamable Carriers Containing Polyols

| Ingredient | TECH PG-026 % W/W | TECH PG-027 % W/W | TECH PG-028 % W/W |
|---|---|---|---|
| Stearyl alcohol | 2.00 | 1.00 | 1.00 |
| Propylene glycol (PG) | 76.00 | 46.00 | 78.00 |
| Laureth-4 | 2.00 | 2.00 | 2.00 |
| Glyceryl stearate (and) PEG-100 stearate (Simulsol 165) | | 1.50 | |
| Glycerin anhydrous | | 33.00 | |
| Hydroxypropylcellulose (Klucel EF) | 2.00 | 1.50 | 1.50 |
| Dimethyl isosorbide (DMI) | 15.00 | 15.00 | 15.00 |
| Glyceryl stearate | 1.00 | | 1.00 |
| Ceteareth-6 (and) stearyl alcohol (Macrogol cetostearyl ether) | 2.00 | | 1.50 |
| Total | 100.00 | 100.00 | 100.00 |
| Foam quality | Excellent | Excellent | Excellent |

Notes:

Composition TECH PG-027 demonstrates that a mixture of two polyols (PG and glycerin, plus DMI (secondary polar solvent) maintains Exellent foam quality. This composition possesses high skin hydration effect. It further possesses high skin penetration enhancing properties.

The liquefied or gas propellant can be added at a concentration of about 3% to about 25%.

EXAMPLE 4

Additional Foamable Carriers Containing Polyols having Excellent Foam Structure

| Ingredient | TECH-PG 029 % w/w | TECH-PG 030 % w/w | TECH-PG 031 % w/w | TECH-PG 032 % w/w | TECH-PG 033 % w/w |
|---|---|---|---|---|---|
| Propylene Glycol | 91.0 | 58.0 | 43.0 | 46.0 | 78.0 |
| Stearyl Alcohol | 2.0 | 1.0 | 1.0 | 1.0 | 1.0 |
| Glycerin | — | 33.0 | 33.0 | 33.0 | — |
| Klucel EF | 2.0 | 3.0 | 3.0 | 1.5 | 1.5 |
| Laureth-4 | 2.0 | 2.0 | 2.0 | 2.0 | 2.0 |
| Simulsol 165 | 3.0 | 3.0 | 3.0 | 1.5 | — |
| Dimethyl Isosorbide | — | — | 15.0 | 15.0 | 15.0 |
| Macrogol Cetostearyl Ether | — | — | — | — | 1.5 |
| Glyceryl Stearate | — | — | — | — | 1.0 |

EXAMPLE 5

Foamable Polyols Compositions, Containing Steroid Drugs

The following steroids were included in formulations were included in formulations TECH-PG30,31 and 33: bethamethasone valerate 0.12%, clobetasol propionate 0.05%, bethamethasone dipropionate 0.05%, fluocinolone acetonide 0.025%, hydrocortison acetate 0.5% and hydrocortison butyrate 0.1%. All samples were stored at 50° C. for 4 weeks, in order to assess their stability. The followinf table provides the results of this short-term stability study, which indicated high compatibility between the polyol composition and the steroid drugs, which are known to be temperature-sensitive.

| | % Degradation after 4 weeks at 50° C. | |
|---|---|---|
| | TECH-PG 032 | TECH-PG 033 |
| Bethamethasone Valerate 0.12% | 1.8% | 1.7% |
| Clobetasol Propionate 0.05% | 4.2% | 5.0% |
| Bethamethasone Dipropionate 0.05% | 0 | 0 |
| Fluocinolone Acetonide 0.025% | 1.3% | 1.7% |
| Hydrocortison Acetate 0.5% | 1.6% | 2.1% |
| Hydrocortison Butyrate 0.1% | 2.6% | 2.8 |

EXAMPLE 6

Foamable Polyol Pharmaceutical Composition Comprising a Combination of Betamethasone Dipropionate and Calcipotriol

| Ingredient | FXCLB1 % W/W | FXCLB2 % W/W |
|---|---|---|
| Propylene glycol | 90.945 | 77.945 |
| Stearyl alcohol | 2.00 | 1.00 |
| Klucel EF | 2.00 | 1.50 |
| Laureth-4 | 2.00 | 2.00 |
| Simulsol 165 | 3.00 | |
| Macrogol Cetostearyl Ether | | 1.50 |
| Glyceryl Stearate | | 1.00 |
| Dimethyl isosorbide | | 15.00 |
| Calcipotriol | 0.005 | 0.005 |
| Betamethasone Dipropionate | 0.05 | 0.05 |

Notes:

Composition FXCLB1 and FXCLB2 contain two active agents (a corticosteroid and a vitamin D derivative, which are known ot exert a synergistic therapeutic effect in psoriasis. These compositions contribute to enhanced skin penetration of the active agents.

The liquefied or gas propellant can be added at a concentration of about 3% to about 25%.

EXAMPLE 7

Foamable Polyol Pharmaceutical Composition Comprising Acyclovir

| Ingredient | % W/W |
|---|---|
| Acyclovir | 5.00 |
| Propylene Glycol | 43.70 |
| Stearyl Alcohol | 0.95 |
| Glycerin | 31.35 |
| Hydroxypropyl cellulose | 1.43 |
| Laureth-4 | 1.90 |
| Glyceryl Monostearate/PEG 100 Stearate | 1.43 |
| Dimethyl Isosorbide | 14.25 |

Notes:

The composition contains acyclovir, which is not fully soluble in the plyol and DMI mixture. However, due to the unique composition, the acyclovir does not readily precipitate and does not undergo caking. Furthermore, thanks to the low viscosity of the composition, upon shaking the active agent readily re-disperses in the composition, resulting in full formulation uniformity.

The combination of polyols and dimethyl isosorbide contributes to enhanced skin bioavailability of the active agent.

The liquefied or gas propellant can be added at a concentration of about 3% to about 25%.

EXAMPLE 8

Foamable Compositions Containing Polyethylene Glycol

|  | % w/w | % w/w | % w/w | % w/w | % w/w | % w/w | % w/w |
|---|---|---|---|---|---|---|---|
| PEG400 | 87.50 | 91.50 | 87.50 | 89.50 | 87.50 | 87.50 | 87.50 |
| Klucel MX (hydroxypropyl cellulose) | 0.50 | 0 | 0.50 | 0 | 0.50 | 0 | 0.50 |
| Klucel LF (hydroxypropyl cellulose) | 0 | 0.50 | 0 | 0.50 | 0 | 0.50 | 0 |
| Lipocol C2 (POE (2) cetyl ether) | 2.00 | 2.00 | 0 | 0 | 0 | 0 | 0 |
| Myrj 52 | 0 | 0 | 2.00 | 2.00 | 0 | 0 | 0 |
| Steareth-2 | 0 | 0 | 0 | 0 | 2.00 | 2.00 | 0 |
| Dermofeel G10L (Polyglyceryl-10 Laurate) | 0 | 0 | 0 | 0 | 0 | 0 | 2.00 |
| Propellant | 10 | 6 | 10 | 8 | 10 | 10 | 10 |
| Density | 0.060 | 0.063 | 0.063 | 0.055 | 0.052 | 0.050 | 0.075 |

Notes:

The liquefied or gas propellant can be added at a concentration of about 3% to about 25%.

The foams of this example have a non-ionic surface active agent at a concentration of 2%. Total amounts of surface active agent foam adjuvant and polymeric agent is in the range of 2.5%.

The compositions are useful as carriers of various active therapeutic active agents.

EXAMPLE 9

Foamable Hygroscopic Compositions, Containing Mupirocin

The following table exemplifies the use of PEG as a hygroscopic substance, which also serves as an effective solvent for Mupirocin, which is practically insoluble in mineral oil and other commonly used ointment solvents. Note that Mupirocin is incompatible with most solvents and thus, a foam comprising PEG as the sole solvent is highly valuable.

|  | % w/w | % w/w | % w/w |
|---|---|---|---|
| Mupirocin | 2.00 | 2.00 | 2.00 |
| PEG400 | 89.50 | 89.50 | 89.50 |
| Hydroxypropyl cellulose | 0.50 | 0.50 | 0.50 |
| Steareth-2 | 2.00 | 1.00 | 0 |
| Polyglyceryl-10 Laurate |  |  | 2.00 |
| Propellant (Propane/butane)* | 6.0 | 6.0 | 6.0 |
| Density | 0.060 | 0.060 | 0.062 |

Notes:

The liquefied or gas propellant can be added at a concentration of about 3% to about 25%.

The foams of this example have a non-ionic surface active agent at a concentration of 2%. Total amounts of surface active agent foam adjuvant and polymeric agent is in the range of 2.5% (w/w).

EXAMPLE 10

Foamable Hygroscopic Compositions, Containing Terbinafine

The following table exemplifies the use of PEG as a hygroscopic substance, which also serves as an effective solvent for terbinafine, which is hard to dissolve in common formulation excipients.

|  | % w/w | % w/w | % w/w |
|---|---|---|---|
| Terbinafine | 2.00 | 2.00 | 6.00 |
| PEG400 | 89.50 | 89.50 | 89.50 |
| Hydroxypropyl cellulose | 0.50 | 0.50 | 0.50 |
| Steareth-2 | 2.00 | 1.00 | 0 |
| Polyglyceryl-10 Laurate |  |  | 2.00 |
| Propellant (Propane/butane)* | 6.0 | 6.0 | 6.0 |
| Density | 0.060 | 0.060 | 0.062 |

EXAMPLE 11
Comparative in-vitro Activity of a Hygroscopic Composition Containing Terbinafine A comparative in-vitro study was set to evaluate the effect of Composition A, consisting of 2% terbinafine, 95.3% gr. polyethylene glycol, 0.5% hydroxypropyl cellulose and 2.2% steareth-2, in comparison with Composition B (an oil in water emulsion containing 2% terbinafine) and Composition C a commercial 1% bifonazole cream.

Three fungal strains (*microsporum canis, trichophyton mentagrophytes* and *trichophyton rubrum*) and one yeast (*candida albicans*) were seeded in the center of a Petri dish, and then, were surrounded by a film containing each of the compositions, using a swab, soaked with each of the compositions. The proliferation and spreading of the microorganisms was followed up for 14 day by visual and photographic observations.

Figure 1:
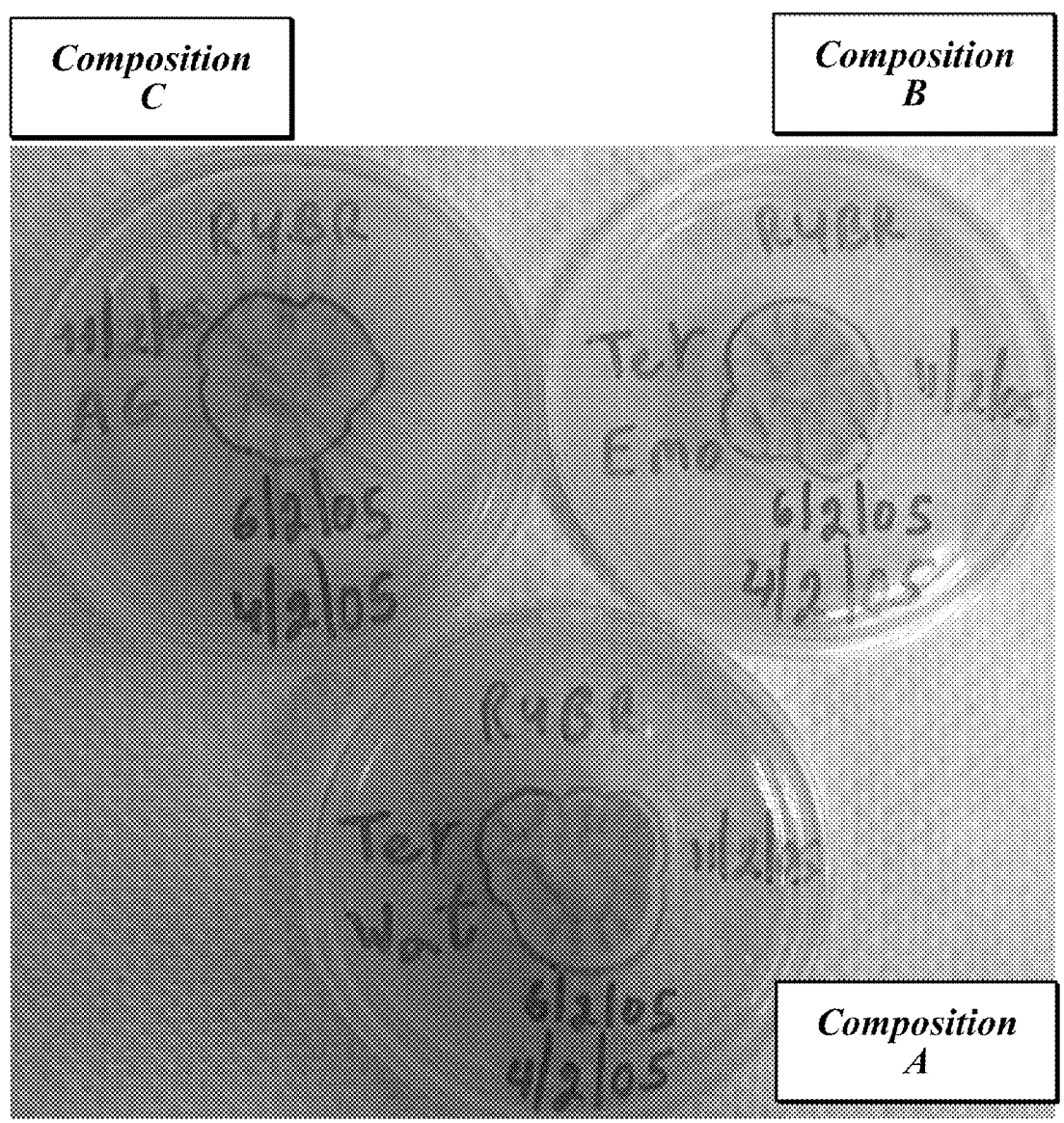

As shown in FIG. 1, Composition A inhibited the proliferation and spreading of all the fungal and yeast strains effectively. By contrast, both Compositions B and C failed to inhibit the growth of *candida*. Composition C was also ineffective in the inhibition of *microsporum canis* and *Trichophyton rubrum*.

EXAMPLE 12

Foamable Hygroscopic Composition Containing Dimethyl Isosorbide

|  | % w/w | % w/w | % w/w | % w/w |
|---|---|---|---|---|
| Oleyl alcohol | 2.50 | — | — | — |
| IPM | 5.00 | 5.00 | 5.00 | — |
| Caprylic/Capric Triglyceride (MCT oil) | 5.00 | 5.00 | 5.00 | 46.00 |
| Epikuron P100 | — | — | — | 10.00 |
| PPG-15 stearyl ether | — | — | — | 2.00 |
| Sorbitane stearate | 8.00 | 8.00 | 8.00 | 2.00 |
| Glyceryl monostearate | — | 1.00 | 1.00 | 1.00 |
| Stearyl alcohol | — | 5.00 | 5.00 | — |
| Cetostearyl alcohol | 8.00 | — | — | — |
| Klucel MF | — | 0.50 | — | — |
| PVP K-90 | — | — | — | 0.50 |
| Sisterna SP50 | 5.00 | 8.00 | 8.00 | — |
| Propylene glycol | 2.50 | — | — | — |
| DMI | 55.50 | 59.00 | 59.50 | 20.00 |
| Water pure | — | — | — | 10.00 |
| Phenonip | 0.50 | 0.50 | 0.50 | 0.50 |
| Propellant | 8.00 | 8.00 | 8.00 | 8.00 |

EXAMPLE 13

Hygroscopic Antifungal Compositions

|  | Ointment Type | | | Lacquer Type | | |
|---|---|---|---|---|---|---|
|  | % w/w | % w/w | % w/w | % w/w | % w/w | % w/w |
| PEG 400 | 92.00 | 92.00 | 93.00 | — | 54.00 | 46.00 |
| PEG 4000 | 6.00 | — | — | — | — | — |
| PEG 6000 | — | 6.00 | 6.00 | — | 10.00 | 8.00 |
| Ethyl acetate/Isopropanol | — | — | — | 30.00 | 30.00 | 30.00 |
| Urea | — | — | — | — | — | 10.00 |
| Terbinafine | 2.00 | 2.00 | — | 2.00 | 4.00 | — |
| Ciclopirox | — | — | 1.00 | — | — | 4.00 |

The lacquer type compositions are suitable for the treatment of infected cornified tissues, and particularly the nail.

Example 14

Comparison Between Polyethylene-Based Foamable Compositions with and without Gelling Agent The compositions of the test articles are provided in the following table. All foams were dispensed on a warm surface (38° C.), and the time to full collapse of the foam was measured. As shown in the table, it has been strikingly demonstrated that foam compositions without a gelling agent exhibit a 100% breakdown within 30 seconds, while foams containing gelling agent remained, with and without surfactant, were stable for several minutes. This is relevant from the usability point of view, since a foam that is unstable at skin temperature cannot be applied to large areas affectively.

|  | Formulations without gelling agent | | | | Formulation with gelling agent | |
|---|---|---|---|---|---|---|
|  | PG33 % w/w | PG34 % w/w | PG35 % w/w | PG36 % w/w | TEC49 % w/w | PG29 % w/w |
| PEG 400 | 87.25 | 93.00 | 91.00 | 92.00 | 90.50 | 93.50 |
| Klucel GF (gelling agent) | — | — | — | — | 0.50 | 0.50 |
| Ceteareth-15 | — | — | 2.00 | 1.00 | — | — |
| Emulsiying Wax NF | 1.80 | — | — | — | — | — |
| Steareth-10 | — | 0.40 | — | 0.50 | — | — |
| PEG-40 stearate | 1.35 | — | — | — | — | — |
| Steareth-2 | — | 0.60 | 1.00 | 0.50 | 1.00 | — |
| Span 60 | 2.70 | — | — | — | — | — |
| Polysorbate 60 | 0.90 | — | — | — | — | — |
| Propellant | 6.00 | 6.00 | 6.00 | 6.00 | 8.00 | 6.00 |
| Collapse time (Seconds; 38° C.) | <30 | <30 | <30 | <30 | 240 | >300 |

EXAMPLE 15

Foamable Hygroscopic Composition Containing Polyethylene Glycol with no Surfactant

|  | % w/w |
| --- | --- |
| PEG 400 | 93.50 |
| Klucel GF | 0.50 |
| Propellant (Butane/propane) | 6.00 |
| Foam quality | E |
| Density | 0.09 |

What is claimed is:

1. A hygroscopic pharmaceutical composition in a pressurized container comprising:
   a. at least one hygroscopic substance at a sufficient concentration to provide an Aw value of the hygroscopic pharmaceutical composition of less than 0.9, wherein the hygroscopic substance comprises a polyethylene glycol (PEG) or a polyol;
   b. an anti-infective agent;
   c. about 0.01% to about 5% by weight of at least one polymeric agent, wherein the polymeric agent is a gelling agent;
   d. about 0.2% to about 5% by weight of a surface-active agent; and
   e. a liquefied or compressed gas propellant;
   wherein the composition comprises not more than 10% or about 10% water by weight; and
   wherein the composition forms a breakable foam upon dispensing from the pressurized container.

2. The composition of claim 1, wherein the Aw value of the composition ranges from about 0.7 to about 0.9.

3. The foamable pharmaceutical carrier of claim 1, wherein the composition is substantially non-aqueous.

4. The foamable carrier of claim 1, wherein the composition is substantially free of short-chain alcohols.

5. A foamable pharmaceutical carrier in a pressurized container comprising:
   a. about 50% to about 98% of a polar solvent selected from the group consisting of (1) a polyol and (2) a polyethylene glycol (PEG);
   b. 0% to about 48% of a secondary polar solvent;
   c. about 0.2% to about 5% by weight of a surface-active agent;
   d. about 0.01% to about 5% by weight of at least one polymeric agent selected from a bioadhesive agent, a gelling agent, a film forming agent and a phase change agent; and
   e. a liquefied or compressed gas propellant at a concentration of about 3% to about 25% by weight of the total composition;
   wherein the carrier comprises not more than 10% or about 10% water by weight and wherein the carrier forms a breakable foam upon dispensing from the pressurized container.

6. The foamable carrier of claim 5, wherein the carrier is substantially non-aqueous.

7. The foamable carrier of claim 5, wherein the polyol comprises a diol, or a triol.

8. The foamable carrier of claim 7, wherein the diol is selected from the group consisting of propylene glycol, butanediol, butenediol, butynediol, pentanediol, hexanediol, octanediol, neopentyl glycol, 2-methyl-1,3-propanediol, diethylene glycol, triethylene glycol, tetraethylene glycol, dipropylene glycol and dibutylene glycol.

9. The foamable carrier of claim 7, wherein the triol is selected from the group consisting of glycerin, butane-1,2,3-triol, butane-1,2,4-triol and hexane-1,2,6-triol.

10. The foamable carrier of claim 5, wherein the polyol comprises at least one diol and at least one triol, and wherein the ratio between the diol and triol is between 9:1 and 1:1.

11. The foamable carrier of claim 5, wherein the PEG is selected from the group consisting of PEG 200, PEG 300, PEG 400, PEG 600, PEG 1000, PEG 4000, PEG 6000 and PEG 8000.

12. The foamable carrier of claim 5, wherein the foamable carrier comprises one or more PEGs in a concentration to provide viscosity of less than 12,000 CPs.

13. The foamable carrier of claim 5, wherein the carrier composition comprises a mixture of at least one polyol and at least one PEG.

14. The foamable carrier of claim 5, wherein the secondary polar solvent is selected from the group consisting of dimethyl isosorbide, tetrahydrofurfuryl alcohol polyethyleneglycol, ether, DMSO, a pyrrolidone, N-Methyl-2-pyrrolidone, 1-Methyl-2-pyrrolidinone, ethyl proxitol, dimethylacetamide, a PEG-type surfactant, an alpha hydroxy acid, lactic acid and glycolic acid.

15. The foamable carrier of claim 14, wherein the secondary polar solvent is dimethyl isosorbide.

16. The foamable carrier of claim 5, wherein the carrier composition comprises (1) at least one polar solvent selected from a diol, a triol and PEG, and (2) at least one secondary polar solvent.

17. The foamable carrier of claim 16, wherein the polyol comprises a mixture of at least two polyols.

18. The foamable carrier of claim 5, wherein the polar solvent comprises a mixture of at least one polyol and at least one PEG.

19. The foamable carrier of claim 18, wherein the ratio between the polyol and/or PEG and the secondary polar solvent is between 9:1 and 1:1.

20. The foamable carrier of claim 5, wherein the concentration of the polar solvent and the secondary polar solvent is sufficient to provide an Aw value of the hygroscopic pharmaceutical composition of less than 0.9.

21. The foamable carrier of claim 20, wherein the range of the Aw value of the composition is from about 0.7 to about 0.9.

22. The foamable carrier of claim 5, wherein the composition is substantially free of short-chain alcohols.

23. The foamable carrier of claim 5, wherein the polymeric agent is selected from the group consisting of locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, an amine-bearing polymer, chitosan, alginic acid, hyaluronic acid, a chemically modified starch, a carboxyvinyl polymer, polyvinylpyrrolidone, polyvinyl alcohol, a polyacrylic acid polymer, a polymethacrylic acid polymer, polyvinyl acetate, a polyvinyl chloride polymer, a polyvinylidene chloride polymer, methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxyethylcellulose, a cationic cellulose PEG 1000, PEG 4000, PEG 6000 and PEG 8000.

24. The foamable carrier of claim 5, wherein the polymeric agent is dispersible in the polyol or in the mixture of a polyol and an additional polar solvent.

25. The foamable carrier of claim 5, wherein the polymeric agent is selected from the group consisting of hydroxypropylcellulose and carbomer.

26. The foamable carrier of claim 5, wherein the polymeric agent is a carbomer.

27. The foamable carrier of claim 5, wherein the concentration of the polymeric agent is selected such that the viscosity of the composition is less than 12,000 CPs, or less than 10,000 CPs.

28. The foamable carrier of claim 5, wherein the surface active agent has an HLB value between about 7 and 12.

29. The foamable carrier of claim 5, wherein the surface active comprises at least two surface active agents and the weighted average of their HLB values is between about 7 and about 12.

30. The foamable carrier of claim 29, wherein the surface active agent is selected from the group consisting of PEG 100 stearate, Laureth 4 and cetomacrogol ether.

31. The foamable carrier of claim 5, wherein the composition comprises one or more surface active agents having an HLB value between about 9 and about 14.

32. The foamable carrier of claim 5, wherein the composition comprises one or more surface active agents having an HLB value between about 2 and about 9.

33. The foamable carrier of claim 5, wherein the surface active agent comprises a non-ionic surface active agent.

34. The foamable carrier of claim 5, wherein the surface active agent is selected from the group consisting of a polysorbate, polyoxyethylene (20) sorbitan monostearate, polyoxyethylene (20) sorbitan monooleate, a polyoxyethylene fatty acid ester, a polyoxyethylene alkyl ether, a polyoxyethylene alkyl ether, polyoxyethylene cetyl ether, polyoxyethylene palmityl ether, polyethylene oxide hexadecyl ether, a polyethylene glycol cetyl ether, a sucrose ester, a partial ester of sorbitol, sorbitan monolaurate, sorbitan monolaurate a monoglyceride, a diglyceride, isoceteth-20 and a sucrose ester.

35. The foamable carrier of claim 34, wherein the surface active agent further comprises an ionic surfactant, selected from the group consisting of a cationic surfactant, a zwitterionic surfactant, an amphoteric surfactant and an ampholytic surfactant.

36. The foamable carrier of claim 35, wherein the surface active agent comprises a mixture of at least one non-ionic surfactant and at least one ionic surfactant, wherein the ratio of at least one non-ionic surfactant and at least one ionic surfactant ranges from about 100:1 to about 1:1.

37. The foamable carrier of claim 5, further comprising a hydrophobic solvent.

38. The foamable carrier of claim 37, wherein the hydrophobic solvent is selected from the group consisting of mineral oil, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, unsaturated or polyunsaturated oils, such as olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils; essential oils; and silicone oils, such as dimethicone, cyclomethicone, polyalkyl siloxane, polyaryl siloxane, polyalkylaryl siloxane, a polyether siloxane copolymer and a poly (dimethylsiloxane)-(diphenyl-siloxane) copolymer.

39. The foamable carrier of claim 5, further comprising a foam adjuvant selected from the group consisting of a fatty alcohol, a fatty acid and a hydroxyl fatty acid.

40. The foamable carrier of claim 5, further comprising an additional component selected from the group consisting of an anti perspirant, an anti-static agent, a buffering agent, a bulking agent, a chelating agent, a colorant, a conditioner, a deodorant, a diluent, a dye, an emollient, fragrance, a humectant, an occlusive agent, a penetration enhancer, a perfuming agent, a permeation enhancer, a pH-adjusting agent, a preservative, a skin penetration enhancer, a sunscreen, a sun blocking agent, a sunless tanning agent, and a vitamin.

41. A foamable therapeutic composition in a pressurized container comprising:
   a. a therapeutically effective concentration of an active agent;
   b. about 50% to about 98% of a polar solvent selected from the group consisting of (1) a polyol; and (2) a polyethylene glycol;
   c. 0% to about 48% of a secondary polar solvent;
   d. about 0.2% to about 5% by weight of a surface-active agent;
   e. about 0.01% to about 5% by weight of at least one polymeric agent selected from a bioadhesive agent, a gelling agent, a film forming agent and a phase change agent; and
   f. a liquefied or compressed gas propellant at a concentration of about 3% to about 25% by weight of the total composition.
   wherein the composition comprises not more than 10% or about 10% water by weight and
   wherein, the composition forms a breakable foam upon dispensing from the pressurized container.

42. The foamable therapeutic composition of claim 41, wherein the carrier is substantially non-aqueous.

43. The foamable therapeutic composition of claim 41, wherein the Aw value of the composition ranges from about 0.7 to about 0.9.

44. The foamable therapeutic composition of claim 41, wherein the active agent is selected from the group consisting of active herbal extracts, acaricides, age spot and keratose removing agents, allergen, analgesics, local anesthetics, antiacne agents, antiallergic agents, antiaging agents, antibacterials, antibiotics, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antipsoriatic agents, antirosacea agents antiseborrheic agents, antiseptic, antiswelling agents, antiviral agents, anti-yeast agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, non-steroidal anti-inflammatory agents, oxidizing agents, pediculicides, photodynamic therapy agents, retinoids, sanatives, scabicides, self tanning agents, skin whitening agents, asoconstrictors, vasodilators, vitamins, vitamin D, wound healing agents and wart removers.

45. The foamable therapeutic composition of claim 41, wherein the active agent is selected from the group consisting of alclometasone dipropionate, amcinafel, amcinafide, amcinonide, beclomethasone, beclomethasone dipropionate, betamethsone, betamethasone benzoate, betamethasone dexamethasone-phosphate, dipropionate, betamethasone valerate, budesonide, chloroprednisone, chlorprednisone acetate, clescinolone, clobetasol, clobetasol propionate, clobetasol valerate, clobetasone, clobetasone butyrate, clocortelone, cortisone, cortodoxone, craposone butyrate, desonide, desoxymethasone, dexamethasone, desoxycorticosterone acetate, dichlorisone, diflorasone diacetate, diflucortolone valerate, diflurosone diacetate, diflurprednate, fluadrenolone, flucetonide, flucloronide, fluclorolone acetonide, flucortine butylesters, fludroxycortide, fludrocortisone, flumethasone, flumethasone pivalate, flumethasone pivalate, flunisolide, fluocinolone, fluocinolone acetonide, fluocinonide, fluocortin butyl, fluocortolone, fluorometholone, fluosinolone acetonide, fluperolone, fluprednidene acetate, fluprednisolone hydrocortamate, fluradrenolone, fluradrenolone acetonide, flurandrenolone, fluticasone, halcinonide, halobetasol, hydrocortisone, hydrocortisone acetate, hydrocortisone butyrate, hydrocortisone cyclopentylpropionate, hydrocortisone valerate, hydroxyltriamcinolone, medrysone, meprednisone, alpha-methyl dexamethasone, methylprednisolone, methylprednisolone acetate, mometasone furoate, paramethasone, prednisolone, prednisone, pregnenolone, progesterone, spironolactone, triamcinolone, triamcinolone acetonide esters and salts thereof.

46. The foamable therapeutic composition of claim 43, wherein the active agent is an anti-infective agent.

47. The foamable therapeutic composition of claim 46, wherein the anti-infective agent is selected from the group consisting of an antibiotic agent, an antibacterial agent, an antifungal agent, an agent that controls yeast, an antiviral agent and an antiparasitic agent.

48. The foamable therapeutic composition of claim 47, wherein the antifungal agent is selected from the group consisting of a polyene, natamycin, nystatin; an allylamine, naftifine, terbinafine; an imidazole, bifonazole, clotrimazole, econazole, fenticonazole, ketocanazole, miconazole, oxiconazole; a diazole, a triazole, fluconazole, itraconazole, terconazole, tolnaftate, ciclopirox, undecylenic acid, sulbentine, griseofulvin, Amphotericin B, flucytosine (5FC), a morpholine compound, amorolfine, and salts thereof, and any combination thereof at a therapeutically effective concentration.

49. The foamable therapeutic composition of claim 47, wherein the antifungal agent is terbinafine.

50. The foamable therapeutic composition of claim 47, wherein the antibacterial agent is selected from the group consisting of a beta-lactam antibiotic, an aminoglycoside, an ansa-type antibiotic, an anthraquinone, an azole, metronidazole, an antibiotic glycopeptide, a macrolide, erythromycin, clindamycin, an antibiotic nucleoside, an antibiotic peptide, polymyxin B, an antibiotic polyene, an antibiotic polyether, an antibiotic quinolone, an antibiotic steroid, fucidic acid, mupirocin, chloramphenicol, a sulfonamide, tetracycline, an antibiotic metal, silver, copper, zinc, mercury, tin, lead, bismuth, cadmium, chromium, an oxidizing agent, iodine, iodate, a periodate, a hypochlorite, a permanganate, a substance that release free radicals and/or active oxygen, a cationic antimicrobial agent, a quatemary ammonium compound, a biguanide, chlorhexidine, a triguanide, a bisbiguanide, a polymeric biguanide, a naturally occurring antibiotic compound and salts, ions and complexes thereof.

51. The foamable therapeutic composition of claim 42, wherein the active agent is unstable in the presence of water.

52. The foamable therapeutic composition of claim 41, wherein the active agent is a combination of at least two active agents.

53. The foamable therapeutic composition of claim 42, wherein the active agent is a combination of at least two active agents.

54. The foamable therapeutic composition of claim 41, comprising (1) a corticosteroid; and (2) and active agent selected from the group consisting of an antifungal agent, an antimicrobial agent, an antiviral agent, an anti-acne agent, a vitamin D3, calcipotriol, and antipsoriasis agent, and a keratolytic agent.

55. The foamable therapeutic composition of claim 41, comprising (1) a keratolytic agent; and (2) and active agent selected from the group consisting of a corticosteroid, an antifungal agent, an antimicrobial agent, an antiviral agent, an anti-acne agent, a vitamin D3, calcipotriol, and antipsoriasis agent, an immunomodulator, and immunosuppressant.

56. A method of treating a disorder of mammalian subject, comprising:
   administering a foamable therapeutic composition to a target site, the composition comprising:
   a. a therapeutically effective concentration of an active agent;
   b. about 50% to about 98% of a polar solvent selected from the group consisting of (1) a polyol; and (2) a polyethylene glycol;
   c. 0% to about 48% of a secondary polar solvent;
   d. about 0.2% to about 5% by weight of a surface-active agent;
   e. about 0.01% to about 5% by weight of at least one polymeric agent selected from a bioadhesive agent, a gelling agent, a film forming agent and a phase change agent; and
   f. a liquefied or compressed gas propellant at a concentration of about 3% to about 25% by weight of the total composition;
   wherein the composition comprises not more than 10% or about 10% water by weight; and
   wherein the composition forms a breakable foam upon dispensing from a pressurized container.

57. The method of claim 56, wherein the target site is selected from the group consisting of the skin, a body cavity, a mucosal surface, the nose, the mouth, the eye, the ear canal, the respiratory system, the vagina and the rectum.

58. The method of claim 56, wherein thedisorder is selected from the group consisting of dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, grannuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo, chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum; and wherein the active agent is suitable for treating said disorder.

59. The method of claim 56, wherein the active agent is selected from the group consisting of alclometasone dipropionate, amcinafel, amcinafide, amcinonide, beclomethasone, beclomethasone dipropionate, betamethsone, betamethasone benzoate, betamethasone dexamethasone-phosphate, dipropionate, betamethasone valerate, budesonide, chloroprednisone, chlorprednisone acetate, clescinolone, clobetasol, clobetasol propionate, clobetasol valerate, clobetasone, clobetasone butyrate, clocortelone, cortisone, cortodoxone, craposone butyrate, desonide, desoxymethasone, dexamethasone, desoxycorticosterone acetate, dichlorisone, diflorasone diacetate, diflucortolone valerate, diflurosone diacetate, diflurprednate, fluadrenolone, flucetonide, flucloronide, fluclorolone acetonide, flucortine butylesters, fludroxycortide, fludrocortisone, flumethasone, flumethasone pivalate, flumethasone pivalate, flunisolide, fluocinolone, fluocinolone acetonide, fluocinonide, fluocortin butyl, fluocortolone, fluorometholone, fluosinolone acetonide, fluperolone, fluprednidene acetate, fluprednisolone hydrocortamate, fluradrenolone, fluradrenolone acetonide, flurandrenolone, fluticasone, halcinonide, halobetasol, hydrocortisone, hydrocortisone acetate, hydrocortisone butyrate, hydrocortisone cyclopentylpropionate, hydrocortisone valerate, hydroxyltriamcinolone, medrysone, meprednisone, alpha-methyl dexamethasone, methyiprednisolone, methyiprednisolone acetate, mometasone fiaroate, paramethasone, prednisolone, prednisone, pregnenolone, progesterone, spironolactone, triameinolone, triameinolone acetonide and derivatives, esters and salts thereof.

60. The method of claim 56, wherein the composition is substantially non-aqueous.

61. The method of claim 56, wherein the Aw value of the composition is from about 0.7 to about 0.9.

62. The method of claim 61, wherein the active agent is an anti-infective agent.

63. The method of claim 62, wherein the anti-infective agent is selected from the group consisting of an antibiotic agent, an antibacterial agent, an antifUngal agent, an agent that controls yeast, an antiviral agent and an antiparasitic agent.

64. The method of claim 62, wherein the antifungal agent is selected from the group consisting of a polyene, natamycin, nystatin; an allylamine, naflifine, terbinafine; an imidazole, bifonazole, clotrimazole, econazole, fenticonazole, ketocanazole, miconazole, oxiconazole; a diazole, a triazoles, fluconazole, itraconazole, terconazole, tolnafiate, ciclopirox, undecylenic acid, sulbentine, griseofulvin, Amphotericin B, flucytosine (5FC), a morpholine compound, amorolfine, and the related morpholines and salts thereof, and any combination thereof at a therapeutically effective concentration.

65. The method of claim 62, wherein the antifungal agent is terbinafine.

66. The method of claim 62, wherein the antibacterial agent is selected from the group consisting of a beta-lactam antibiotic, an aminoglycoside, an ansa-type antibiotic, an anthraquinone, an azole, metronidazole, an antibiotic glycopeptide, a macrolide, erythromycin, clindamycin, an antibiotic nucleoside, an antibiotic peptide, polymyxin B, an antibiotic polyene, an antibiotic polyether, an antibiotic quinolone, an antibiotic steroid, fucidic acid, mupirocin, chioramphenicol, a sulfonamide, tetracycline, an antibiotic metal, silver, copper, zinc, mercury, tin, lead, bismuth, cadmium, chromium, an oxidizing agent, iodine, iodate, a periodate, a hypochlorite, a permanganate, a substance that release free radicals and/or active oxygen, a cationic antimicrobial agent, a quatemary ammonium compound, a biguanide, chlorohexidine, a triguanide, a bisbiguanide, a polymeric biguanide, a naturally occurring antibiotic compound and analogs, derivatives, salts, ions and complexes thereof.

67. The method of claim 60, wherein the active agent is unstable in the presence of water.

68. The method of claim 59, wherein the active agent comprises a combination of at least two active agents.

69. The method of claim 60, wherein the active agent comprises a combination of at least two active agents.

70. The method of claim 68, wherein the active agent comprises a combination of (1) a corticosteroid; and (2) and active agent selected from the group consisting of an anti-infective agent, an antifungal agent, an antimicrobial agent, an antiviral agent, an anti-acne agent, a retinoid, a vitamin D3, calcipotriol, and antipsoriasis agent, a keratolytic agent, an anti-proliferative agent, an anti-cancer agent, a non-steroidal anti-inflammatory agent, an immunomodulator, an immunosuppressant and an anti-rosacea agent.

71. The method of claim 68, wherein the active agent comprises a combination of (1) a keratolytic agent; and (2) and active agent selected from the group consisting of a corticosteroid, an anti-infective agent, an antifungal agent, an antimicrobial agent, an antiviral agent, an anti-acne agent, a retinoid, a vitamin D3, calcipotriol, and antipsoriasis agent, an anti-proliferative agent, an anti-cancer agent, a non-steroidal anti-inflammatory agent, an immunomodulator, an immunosuppressant and an anti-rosacea agent.

72. The composition of claim 1, wherein the Aw value of the composition less than 0.7 or about 0.7.

73. The composition of claim 5, wherein the Aw value of the composition less than 0.7 or about 0.7.

74. The composition of claim 41, wherein the Aw value of the composition less than 0.7 or about 0.7.

75. The foamable carrier of claim 1, wherein the polyol comprises a diol, or a triol.

* * * * *